US011064900B2

(12) United States Patent
Lee et al.

(10) Patent No.: US 11,064,900 B2
(45) Date of Patent: Jul. 20, 2021

(54) ULTRA-LOW FIELD NUCLEAR MAGNETIC RESONANCE DEVICE

(71) Applicant: KOREA RESEARCH INSTITUTE OF STANDARDS AND SCIENCE, Daejeon (KR)

(72) Inventors: Seong-Joo Lee, Daejeon (KR); Kiwoong Kim, Daejeon (KR); Jeong-Hyun Shim, Daejeon (KR); Kwon-Kyu Yu, Daejeon (KR); Seong-min Hwang, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 461 days.

(21) Appl. No.: 16/085,488

(22) PCT Filed: Apr. 3, 2017

(86) PCT No.: PCT/KR2017/003616
§ 371 (c)(1),
(2) Date: Sep. 14, 2018

(87) PCT Pub. No.: WO2017/176012
PCT Pub. Date: Oct. 12, 2017

(65) Prior Publication Data
US 2019/0082997 A1  Mar. 21, 2019

(30) Foreign Application Priority Data

Apr. 4, 2016 (KR) .................. 10-2016-0041225

(51) Int. Cl.
*A61B 5/055* (2006.01)
*G01R 33/48* (2006.01)
(Continued)

(52) U.S. Cl.
CPC ............ *A61B 5/055* (2013.01); *A61B 5/0044* (2013.01); *G01R 33/24* (2013.01); *G01R 33/326* (2013.01);
(Continued)

(58) Field of Classification Search
CPC ...... A61B 5/055; A61B 5/0044; G01R 33/24; G01R 33/326; G01R 33/381; G01R 33/445; G01R 33/48; G01R 33/56; G01R 33/421
See application file for complete search history.

(56) References Cited

U.S. PATENT DOCUMENTS 9,921,280 B2  3/2018 Kim et al.
10,028,674 B2  7/2018 Kim et al.
(Continued)

FOREIGN PATENT DOCUMENTS

JP  2009257933 A  11/2009
JP  2015504756 A  2/2015
(Continued)

OTHER PUBLICATIONS

Shim et al., "Strong pulsed excitations using circularly polarized fields for ultra-low field NMR" Journal of Magnetic Resonance 239 (2014) 87-90 (Year: 2014).*
(Continued)

*Primary Examiner* — Amelie R Davis
*Assistant Examiner* — John Denny Li
(74) *Attorney, Agent, or Firm* — Andrew D. Fortney; Central California IP Group, P.C.

(57) ABSTRACT

Provided are an ultra-low field nuclear magnetic resonance device and a method for measuring an ultra-low field nuclear resonance image. The ultra-low field nuclear magnetic resonance device includes an AC power supply configured to supply a current to a measurement target in such a manner
(Continued)

the current flows to the measurement target, magnetic field measurement means disposed adjacent to the measurement target, and measurement bias magnetic field generation means configured to apply a measurement bias magnetic field corresponding to a proton magnetic resonance frequency of the measurement target. A vibration frequency of the AC power supply matches the proton magnetic resonance frequency of the measurement target, and the magnetic field measurement means measures a nuclear magnetic resonance signal generated from the measurement target.

20 Claims, 18 Drawing Sheets

(51) Int. Cl.
| | |
|---|---|
| G01R 33/381 | (2006.01) |
| G01R 33/32 | (2006.01) |
| G01R 33/56 | (2006.01) |
| A61B 5/00 | (2006.01) |
| G01R 33/24 | (2006.01) |
| G01R 33/44 | (2006.01) |
| G01R 33/421 | (2006.01) |

(52) U.S. Cl.
CPC ......... *G01R 33/381* (2013.01); *G01R 33/445* (2013.01); *G01R 33/48* (2013.01); *G01R 33/56* (2013.01); *G01R 33/421* (2013.01)

(56) References Cited

U.S. PATENT DOCUMENTS

| | | | | |
|---|---|---|---|---|
| 2013/0241551 A1* | 9/2013 | Kim | ...................... | A61B 5/055 324/309 |
| 2014/0343397 A1* | 11/2014 | Kim | ........................ | A61B 5/05 600/409 |

FOREIGN PATENT DOCUMENTS

| | | | |
|---|---|---|---|
| KR | 20120055087 A | 5/2012 | |
| KR | 20120078965 A | 7/2012 | |
| KR | 20130088247 A | 8/2013 | |

OTHER PUBLICATIONS

Zotev et al., SQUID-based instrumentation for ultralow-field MRI, Supercond. Sci. Technol. 20 (2007) S367-S373 (Year: 2007).*

Kiwoong Kim et al.; "Biomagnetic Resonance Device and Measuring Method Therefor"; Bibliographic Data of JP2015504756 (A); Feb. 16, 2015; http://worldwide.espacenet.com.

Kiwoong Kim et al.; "Biomagnetic Resonance Device and Measuring Method Therefor"; Bibliographic Data of KR20130088247 (A); Aug. 8, 2013; http://worldwide.espacenet.com.

Kiwoong Kim et al.; "Method for Direct Measurement of Myocardial Electric Abnormality Based on Ultra-Low-Field Nuclear Magnetic Resonance and Apparatus of Ultra-Low-Field Nuclear Magnetic Resonance"; Bibliographic Data of KR20120055087 (A); May 31, 2012; http://worldwide.espacenet.com.

Ki Woong Kim et al.; "Development of Next-generation Measurement Technology for Biomagnetic Resonance"; Korea Research Institute of Standards and Science Research Report; Oct. 2014; pp. 1-140.

Ki Woong Kim et al.; "Development of Next-generation Measurement Technology for Biomagnetic Resonance"; English Translation of pp. 27, 39 and 42; Korea Research Institute of Standards and Science Research Report; Oct. 2014; 7 pages.

International Search Report dated Jul. 19, 2017; International Application No. PCT/KR2017/003616; 4 pgs.; International Searching Authority/Korean Intellectual Property Office; Daejeon, Republic of Korea.

Ki Woong Kim et al.; "Development of Next-generation Measurement Technology for Biomagnetic Resonance"; Korea Research Institute of Standards and Science Research Report; Dec. 2015; 368 pages.

Ki Woong Kim et al.; "Development of Next-generation Measurement Technology for Biomagnetic Resonance"; English Translation of pp. 43, 142, 160-169 and FIG. 3-1-8; Korea Research Institute of Standards and Science Research Report; Dec. 2015; 22 pages.

Ki Woong Kim et al.; "Development of Next-generation Measurement Technology for Biomagnetic Resonance"; Korea Research Institute of Standards and Science Research Report; Oct. 2015; 103 pages.

Ki Woong Kim et al.; "Development of Next-generation Measurement Technology for Biomagnetic Resonance"; English Translation of pp. 23-28; Korea Research Institute of Standards and Science Research Report; Oct. 2015; 12 pages.

* cited by examiner

ULTRA-LOW FIELD NUCLEAR MAGNETIC RESONANCE DEVICE

CROSS-REFERENCE TO RELATED APPLICATIONS

This application is a continuation of and claims priority to PCT/KR2017/003616 filed on Apr. 3, 2017, which claims priority to Korea Patent Application No. 10-2016-0041225 filed on Apr. 4, 2016, the entireties of which are both hereby incorporated by reference.

TECHNICAL FIELD

The present disclosure relates to a current image based on ultra-low field MRI and, more particularly, to magnetic resonance electrical impedance tomography (MREIT) which provides images for an alternating current by resonating a nuclear spin under a measurement bias magnetic field and a modulated magnetic field generated by the alternating current applied by an external alternating current source.

BACKGROUND

Magnetic resonance electrical impedance tomography (MREIT) is a new bioelectrical impedance imaging method developed by a multidisciplinary fusion technology based on mathematics-bioelectromagnetics-biomedical engineering. MREIT may provide in vivo conductivity and current density images without rotating a living body in an MRI apparatus.

Conventional MREIT has been performed in high-field MRI.

According to the present disclosure, there is provided a method for acquiring an MREIT image in an ultra-low field MM in which a strong static magnetic field is separated into a pre-polarizing magnetic field and a measurement bias magnetic field.

SUMMARY

Example embodiments of the present disclosure provide an apparatus and a method for acquiring a current image formed by an external current source using an ultra-low field nuclear magnetic resonance device.

An ultra-low field nuclear magnetic resonance device according to an example embodiment includes an AC power supply configured to supply a current to a measurement target in such a manner the current flows to the measurement target, magnetic field measurement means disposed adjacent to the measurement target, and measurement bias magnetic field generation means configured to apply a measurement bias magnetic field corresponding to a proton magnetic resonance frequency of the measurement target. A vibration frequency of the AC power supply matches the proton magnetic resonance frequency of the measurement target, and the magnetic field measurement means measures a nuclear magnetic resonance signal generated from the measurement target.

In an example embodiment, the ultra-low field nuclear magnetic resonance device may further include pre-polarizing magnetic field generation means configured to apply a pre-polarizing magnetic field to pre-polarize the measurement target. A direction of the pre-polarizing magnetic field may match a direction of the measurement bias magnetic field.

In an example embodiment, the ultra-low field nuclear magnetic resonance device may further include a pre-polarizing magnetic field generation means configured to a pre-polarizing magnetic field to pre-polarize the measurement target and an excitation magnetic field generation means configured to switch a magnetization direction of the measurement target to a direction of the measurement bias magnetic field. A direction of the pre-polarizing magnetic field is perpendicular to the direction of the measurement bias magnetic field, and the excitation magnetic field rotates a direction of the magnetization in the direction of the measurement bias magnetic field.

In an example embodiment, the excitation magnetic field generation means may generate a circularly polarized excitation magnetic field.

In an example embodiment, the ultra-low field nuclear magnetic resonance device may further include a pre-polarizing magnetic field generation means configured to apply a pre-polarizing magnetic field to pre-polarize the measurement target. A direction of the pre-polarizing magnetic field may be perpendicular to the direction of the measurement bias magnetic field. A magnetization direction of the measurement target may be aligned in the direction of the measurement bias magnetic field by reducing a magnitude of the pre-polarizing magnetic field through an adiabatic process while the measurement bias magnetic field is applied.

In an example embodiment, the ultra-low field nuclear magnetic resonance device may further include a gradient magnetic field generation means configured to provide a gradient magnetic field to the measurement target.

A method for measuring an ultra-low field nuclear resonance image includes applying a pre-polarizing magnetic field to pre-polarize a measurement target, applying a measurement bias magnetic field corresponding to a proton magnetic resonance frequency of the measurement target, applying a modulated magnetic field by providing an alternating current of a vibration frequency corresponding to a proton magnetic resonance frequency of the measurement bias magnetic field to the measurement target, applying a gradient magnetic field to the measurement target, measuring a nuclear magnetic resonance signal generated from the measurement target, and obtaining a current image of the measurement target using the nuclear magnetic resonance signal. A vibration frequency of the alternating current may correspond to a vibration frequency of the measurement bias magnetic field corresponding to the proton magnetic resonance frequency of the measurement target.

In an example embodiment, a direction of the pre-polarizing magnetic field may match a direction of the measurement bias magnetic field, and a direction of the modulated magnetic field may be perpendicular to the direction of the measurement bias magnetic field.

In an example embodiment, the method may further include providing an excitation magnetic field to switch a magnetization direction of the measurement target to a direction of the measurement bias magnetic field. A direction of the pre-polarizing magnetic field may be perpendicular to a direction of the measurement bias magnetic field, and the excitation magnetic field may rotate a magnetization aligned in a direction of the pre-polarizing magnetic field in the direction of the measurement bias magnetic field.

In an example embodiment, a direction of the pre-polarizing magnetic field may be perpendicular to the direction of the measurement bias magnetic field, and a magnetization direction of the measurement target may be aligned in the direction of the measurement bias magnetic field by reducing a magnitude of the pre-polarizing magnetic field through an adiabatic process while the measurement bias magnetic field is applied.

In an example embodiment, the excitation magnetic field may be a circularly polarized excitation magnetic field.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
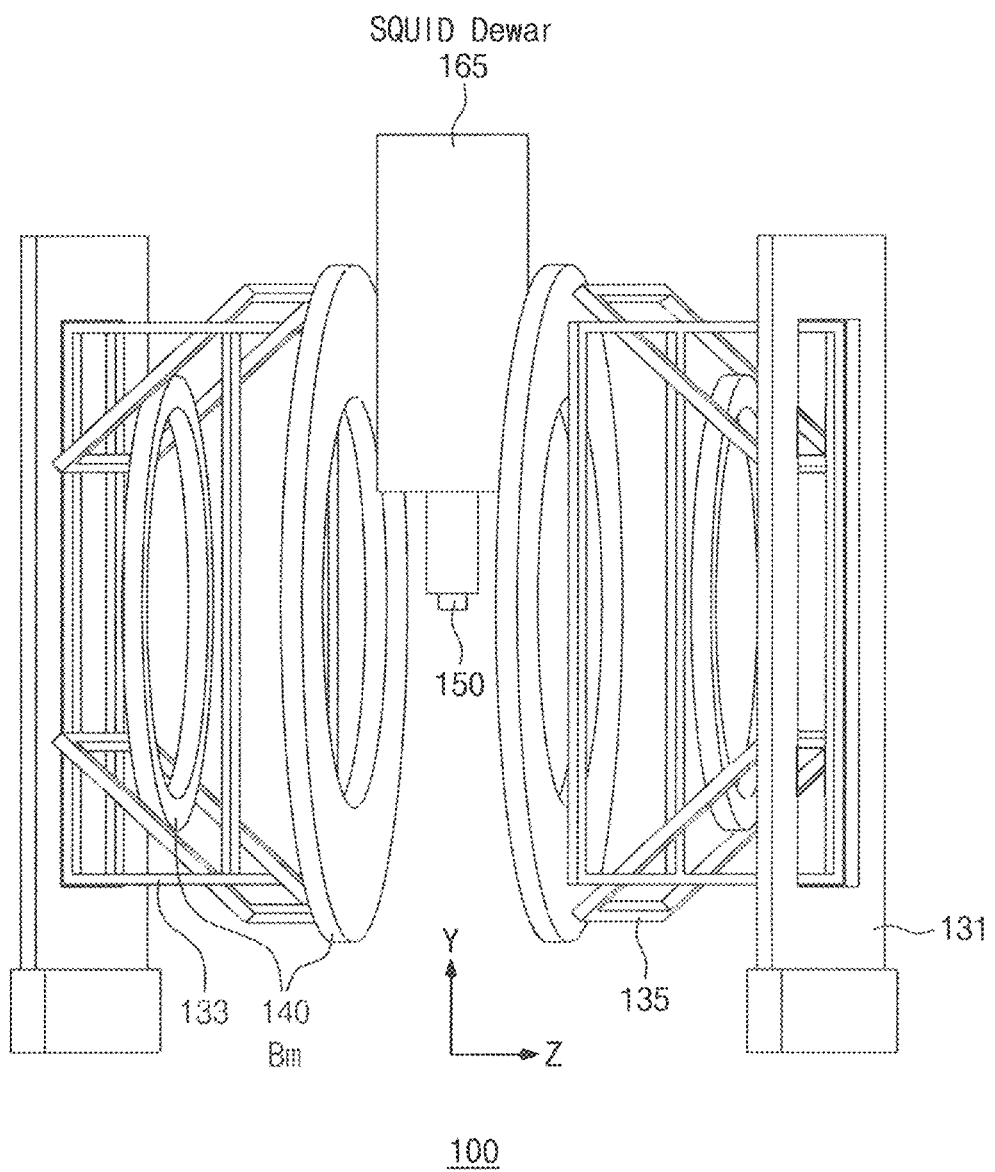
FIG. 1 is a perspective view of a coil structure of an ultra-low field nuclear magnetic resonance device according to an example embodiment of the present disclosure.

A method for acquiring a magnetic resonance electrical impedance tomography (MREIT) image based on ultra-low-field MRI is proposed as a new application technique of biomagnetic resonance. According to the method, low-frequency electric conductivity or current density of a measurement target (an organ in the human body) is measured. Unlike brainwave magnetic resonance (BMR) and heart magnetic resonance (HMR), MREIT is a technique of imaging by using an externally applied current source instead of a human internal current source.

Unlike a conventional high-field MRI based MREIT, an ultra-low field MREIT can measure by direct resonance with a modulated magnetic field generated by an external current source of several tens of Hz to several kHz. Therefore, it is a new method to directly measure the low-frequency electric conductivity or the current density of the internal organs rather than the indirect measurement.

If a vibration frequency of a modulated magnetic field generated by a current applied to a measurement target by an external AC current source matches a magnetic resonance frequency of nuclear magnetization caused by a measurement bias magnetic field, a current map of the measurement target may be measured from a magnetic resonance signal. The current map of the measurement target may acquire a current density image through a deconvolution algorithm. Since the current density is expressed as a product of electric conductivity and an electric field, an electric conductivity image may be acquired from the current density image using an algorithm such as a boundary element method (BEM).

A local part of the measurement target generates a modulated magnetic field $B_{MOD}$ or MOD with a vibration frequency $f_{MOD}$ by an alternating current source. Protons of the measurement target may form protons that cause a resonance with the modulation magnetic field $B_{MOD}$ under a measurement bias magnetic field Bm. The measurement bias magnetic field Bm may be as small as one-millionth of a measurement bias field of conventional magnetic resonance imaging (MM).

In a weak measurement bias magnetic field Bm, it may be difficult to align proton spins. Accordingly, since the magnitude of an actually measured magnetic resonance signal is significantly small, a pre-polarizing magnetic field Bp may be generated during a predetermined interval before the measurement starts. The pre-polarizing magnetic field Bp may pre-polarize a measurement target.

A direction of the pre-polarizing magnetic field Bp may be identical or perpendicular to a direction of the measurement bias magnetic field Bm.

By a strong pre-polarizing magnetic field Bp, protons may be aligned in a direction of a pre-polarizing magnetic field and a measurement target may be magnetized. When the direction of the pre-polarizing magnetic field Bp is perpendicular to a direction of the measurement bias field Bm, a direction of the magnetization may be changed to a direction of the measurement magnetic field Bm by performing an adiabatic process to slowly change the pre-polarizing magnetic field Bp or by applying a separate excitation field B1. To obtain a nuclear magnetic resonance signal, magnetization may precess with a component perpendicular to the measurement bias magnetic field Bm when a modulated magnetic field $B_{MOD}$ having a nuclear magnetic resonance frequency is applied to the measurement target. A magnetization component (or flux component) perpendicular to the measurement bias magnetic field Bm may be measured by a pick-up coil.

When a vibration frequency of the modulation magnetic field $B_{MOD}$ is 1472 Hz, a frequency of the magnetic resonance signal generated by the measurement bias magnetic field Bm may also be 1472 Hz. The magnitude of the magnetic resonance signal may depend on an application time $t_{MOD}$ of the modulated magnetic field $B_{MOD}$ and the intensity of the modulation magnetic field $B_{MOD}$. To obtain a maximum magnetic resonance signal, the application time $t_{MOD}$ of the modulation magnetic field $B_{MOD}$ may be selected under the modulated magnetic field $B_{MOD}$ with constant magnitude. A magnetic resonance image is converted into a current density image using a predetermined algorithm, and the current density image may be converted into an electric conductivity image using a predetermined algorithm.

Example embodiments of the present disclosure will now be described below more fully with reference to accompanying drawings. The present disclosure may, however, be embodied in different forms and should not be constructed as limited to the embodiments set forth herein. Rather, these embodiments are provided so that this disclosure will be thorough and complete, and will fully convey the scope of the present invention to those skilled in the art.

Reference numerals are indicated in detail in example embodiments of the present disclosure, and their examples are represented in reference drawings. In every possible case, like reference numerals are used for referring to the same or similar elements in the description and drawings.

FIG. 1 is a perspective view of a coil structure of an ultra-low field nuclear magnetic resonance device according to an example embodiment of the present disclosure.

Figure 2:
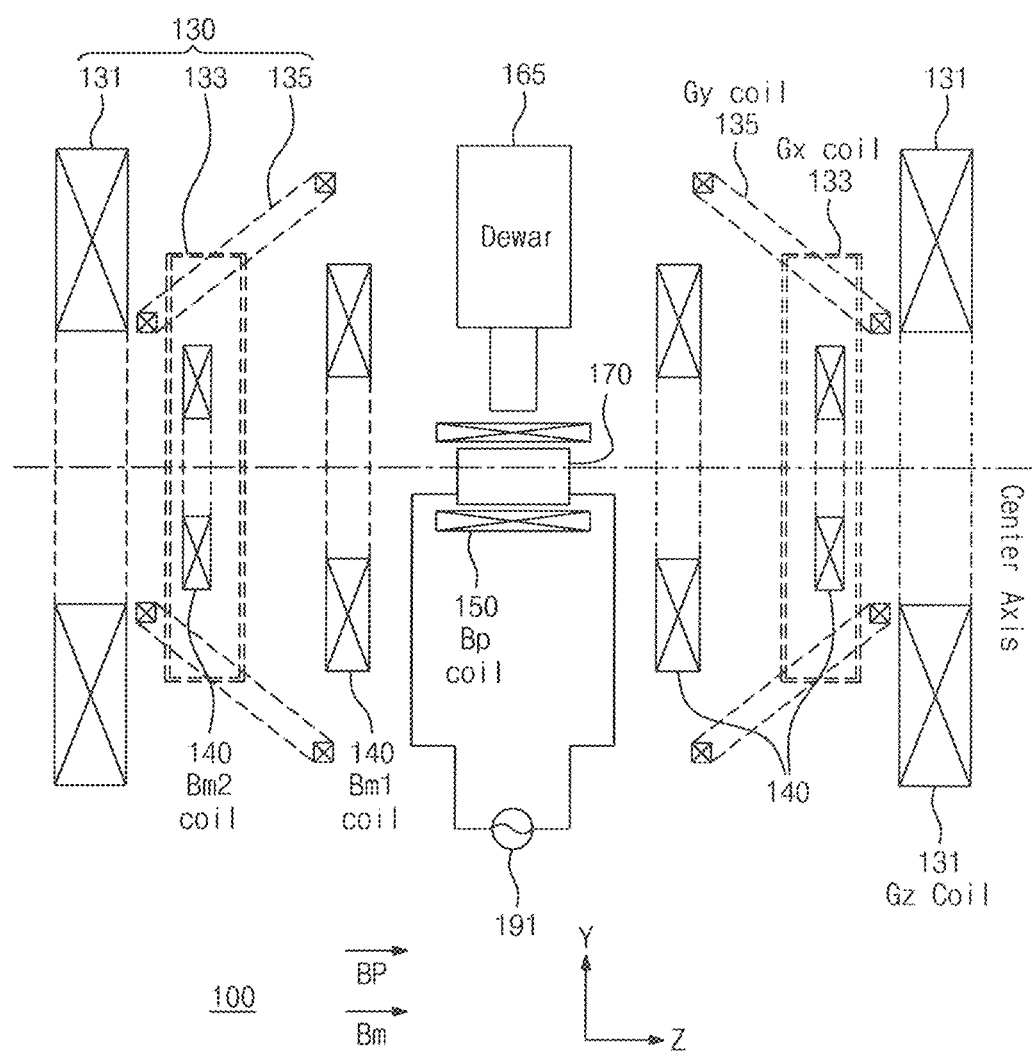
FIG. 2 is a conceptual diagram of the coil structure of the ultra-low field nuclear magnetic resonance device in FIG. 1.

FIG. 2 is a conceptual diagram of the coil structure of the ultra-low field nuclear magnetic resonance device in FIG. 1.

Figure 3:
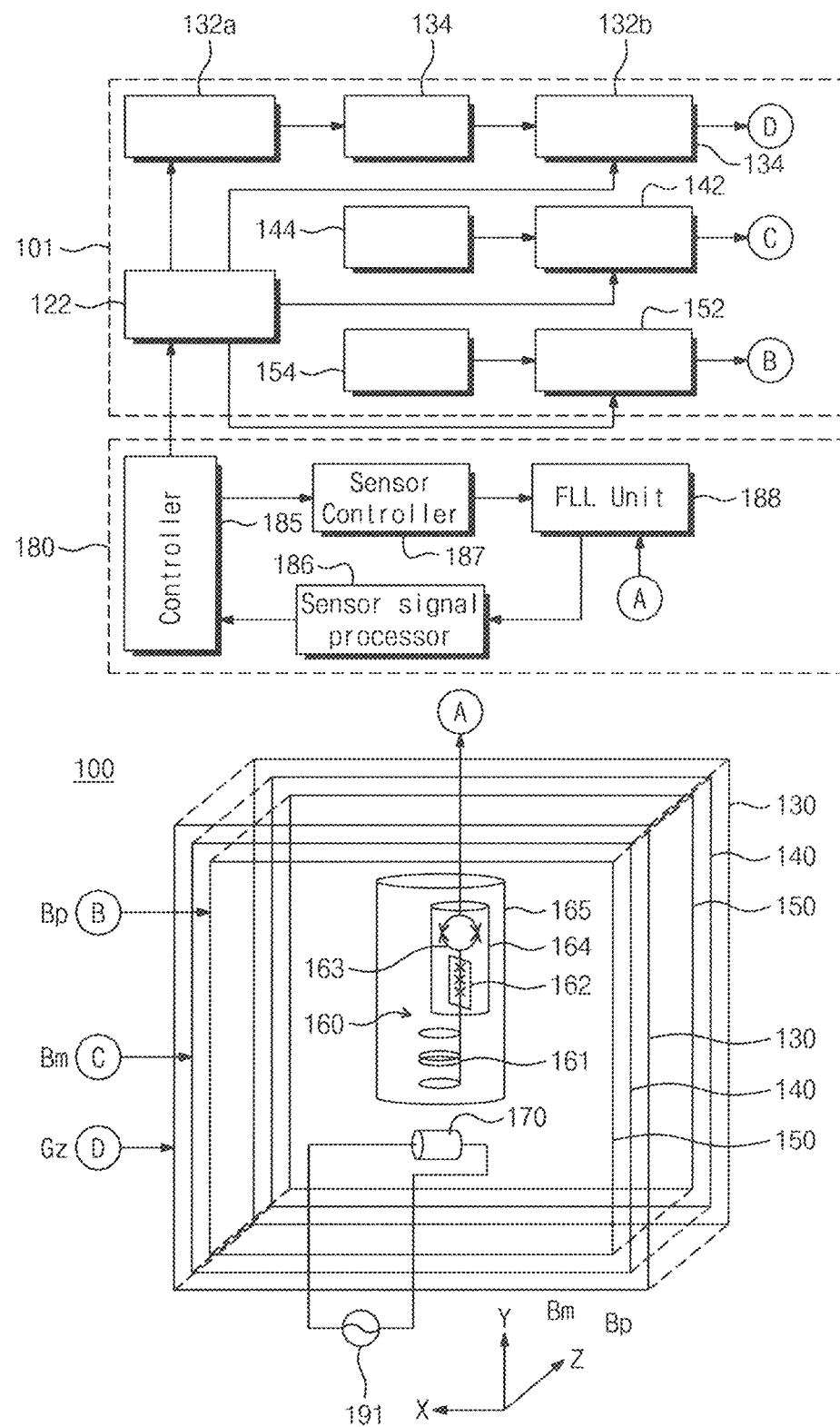
FIG. 3 is a conceptual diagram of the ultra-low field nuclear magnetic resonance device in FIG. 1.

FIG. 3 is a conceptual diagram of the ultra-low field nuclear magnetic resonance device in FIG. 1.

Figure 4:
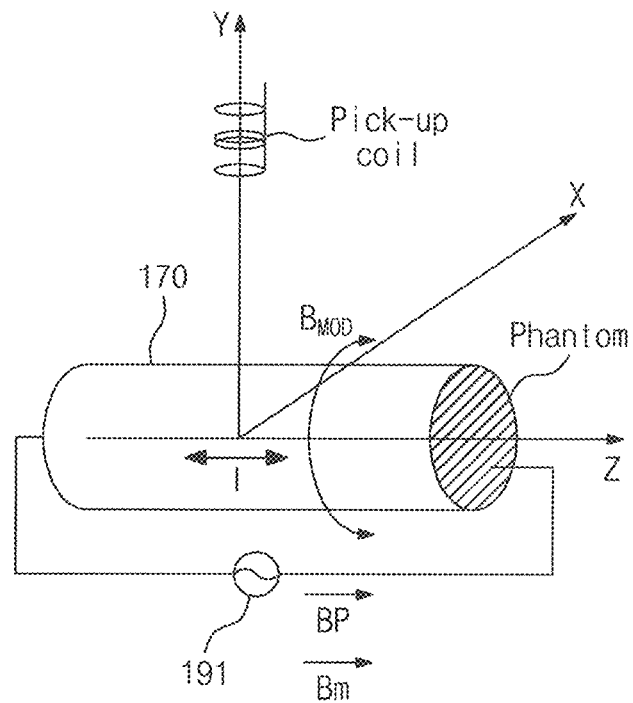
FIG. 4 is a conceptual diagram of a measurement target and a magnetic field direction of the ultra-low field nuclear magnetic resonance device in FIG. 1.
Figure 4:
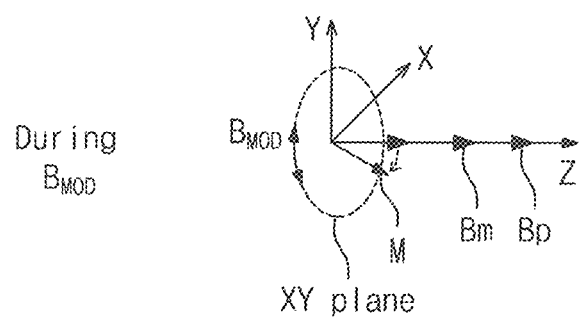
Figure 4:
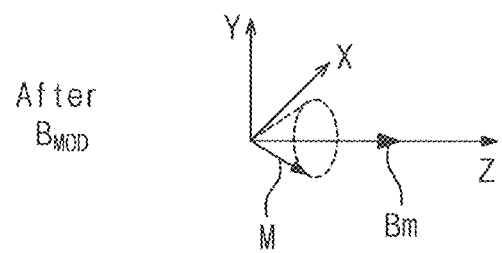

FIG. 4 is a conceptual diagram of a measurement target and a magnetic field direction of the ultra-low field nuclear magnetic resonance device in FIG. 1.

Figure 5:
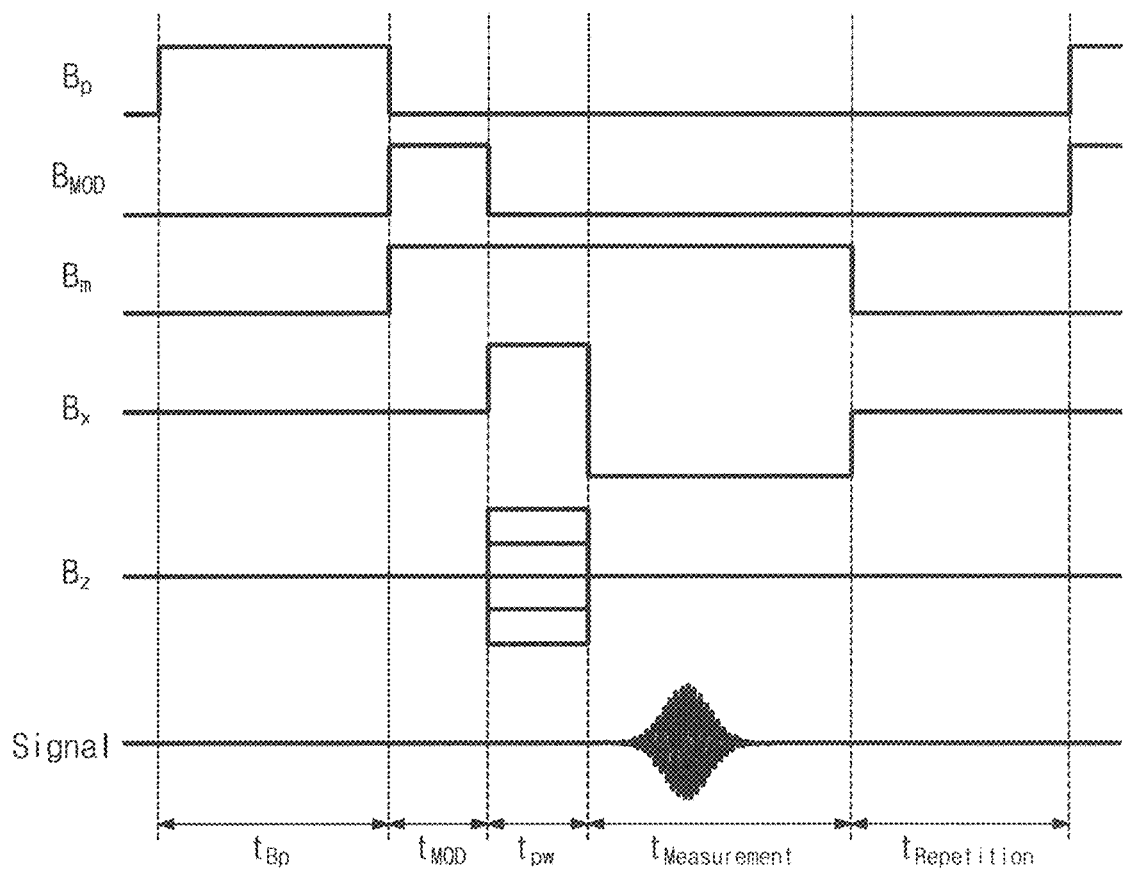
FIG. 5 is a timing chart illustrating a pulse sequence of the ultra-low field nuclear magnetic resonance device in FIG. 1.

FIG. 5 is a timing chart illustrating a pulse sequence of the ultra-low field nuclear magnetic resonance device in FIG. 1.

Figure 6:
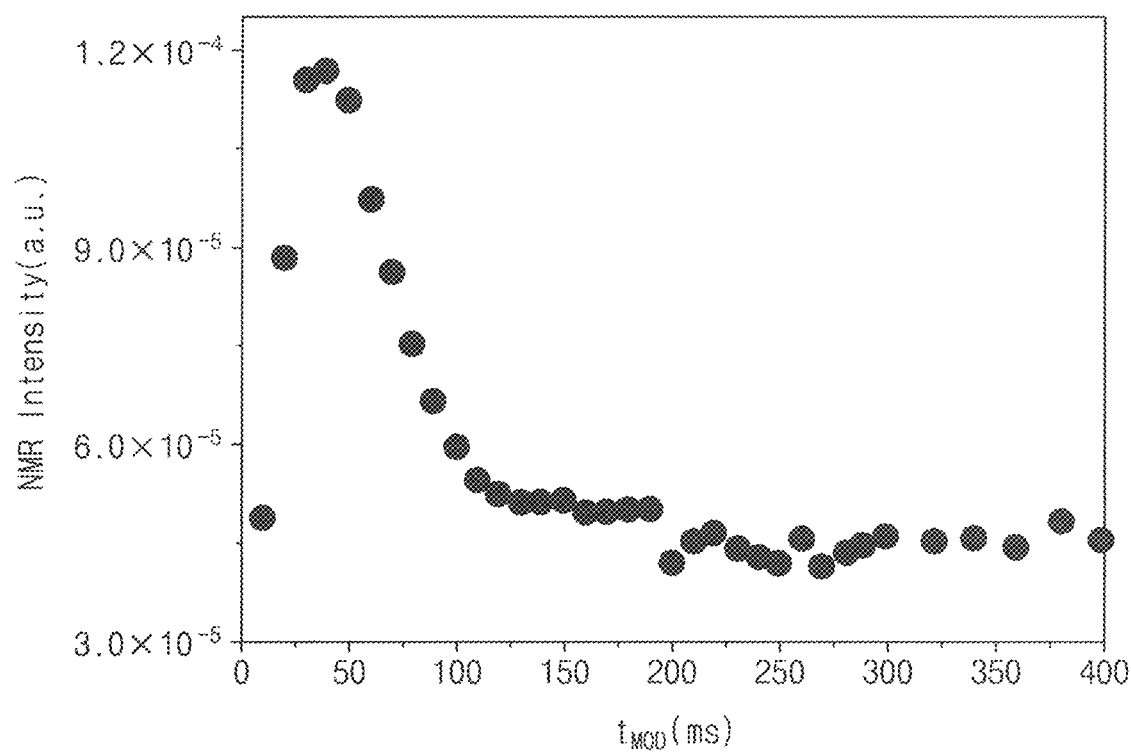
FIG. 6 shows a test result illustrating the intensity of a nuclear magnetic resonance (NMR) signal depending on an application time $t_{MOD}$ of a modulated magnetic field $B_{MOD}$ in the pulse sequence in FIG. 5.

FIG. 6 shows a test result illustrating the intensity of a nuclear magnetic resonance (NMR) signal depending on an application time $t_{MOD}$ of a modulated magnetic field $B_{MOD}$ in the pulse sequence in FIG. 5.

Figure 7:
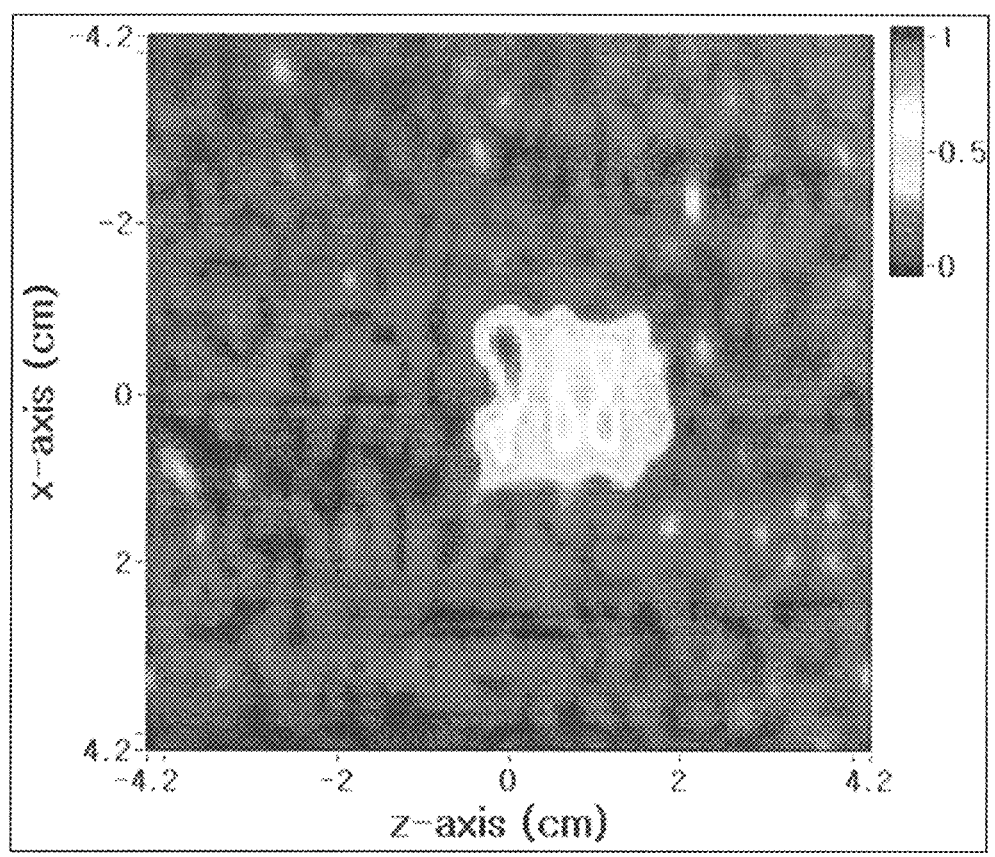
FIG. 7 shows a nuclear magnetic resonance (NMR) image when a modulated magnetic field $B_{MOD}$ is applied in the pulse sequence in FIG. 5.

FIG. 7 shows a nuclear magnetic resonance (NMR) image when a modulated magnetic field $B_{MOD}$ is applied in the pulse sequence in FIG. 5.

Referring to FIGS. 1 to 7, an ultra-low field nuclear magnetic resonance device 100 includes an AC power supply 191 configured to supply a current to a measurement target 170 in such a manner the current flows to the measurement target 170, magnetic field measurement means 160 disposed adjacent to the measurement target 170, and measurement bias magnetic field generation means 140 configured to apply a measurement bias magnetic field Bm corresponding to a proton magnetic resonance frequency of the measurement target 170. A vibration frequency $f_{MOD}$ of the AC power supply 191 matches the proton magnetic resonance frequency of the measurement target 170 and the magnetic field measurement means 160 measures a nuclear magnetic resonance signal generated from the measurement target 170.

A pre-polarizing magnetic field generation means 150 applies a pre-polarizing magnetic field Bp to pre-polarize the measurement target. A direction of the pre-polarizing magnetic field Bp may match a direction of the measurement bias magnetic field Bm.

The measurement target 170 may be a part of the human body. An alternating current may be allowed to flow to the measurement target by an electrode pad. The alternating current flowing to the measurement target 170 generates a modulated magnetic field $B_{MOD}$ having a predetermined vibration frequency $f_{MOD}$. The modulated magnetic field $B_{MOD}$ causes nuclear magnetic resonance with protons under the measurement bias magnetic field Bm.

The AC power supply 191 includes an arbitrary function generator which may generate a sine wave having a predetermined vibration frequency $f_{MOD}$ to apply an AC current to the measurement target 170. An intensity of the alternating current flowing to the measurement target 170 may be in proportion to a voltage of the arbitrary function generator.

The ultra-low field nuclear magnetic resonance device 100 includes magnetic field measurement means 160 disposed adjacent to the measurement target 170 and applies a measurement bias magnetic field Bm corresponding to a magnetic resonance frequency matching a vibration frequency of an alternating current flowing inside the measurement target 170.

The magnetic field measurement means 160 measures magnetic a resonance signal generated from the measurement target 170. The magnetic field measurement means 160 may be a superconducting quantum interference device (SQUID) whose measurement sensitivity is independent of a signal frequency.

The measurement bias magnetic field generation means 140 may generate a measurement bias magnetic field Bm and may be conventional double Helmholtz resistive coils. The measurement bias magnetic field generation means 140 may be disposed inside magnetic shielding means. The measurement bias magnetic field generation means 140 may apply a uniform magnetic field in z-axis direction. Thus, the magnitude of the measurement bias magnetic field Bm may be adjusted to correspond to a vibration frequency $f_{MOD}$ of an alternating current of the measurement target 170. The measurement bias magnetic field Bm may be applied continuously or in the form of a pulse in the z-axis direction.

The pre-polarizing magnetic field generation means 150 generates a pre-polarized magnetic field Bp to pre-polarize the measurement target 170. The pre-polarizing magnetic field generation means 150 may be a conventional resistive coil or a superconducting coil. The pre-polarizing magnetic field generation means 150 may be a solenoid coil that extends in the z-axis direction and is disposed inside the magnetic shielding means. Also, the pre-polarizing magnetic field generation means 150 may surround the measurement target 170 and be disposed inside the measurement bias magnetic field generation means 140. The pre-polarized magnetic field Bp may be applied in the form of a pulse in the z-axis direction.

Gradient magnetic field generation means 130 provides a gradient magnetic field to the measurement target 170. Accordingly, a nuclear magnetic resonance signal generated from the measurement target 170 may be localized. The gradient magnetic field generation means 130 may be a conventional resistive coil. The gradient magnetic field generation means 130 may be disposed between the measurement target 170 and the magnetic shielding means. The gradient magnetic field generation means 130 may generate at least one of an x-axis gradient magnetic field Gx, a y-axis gradient magnetic field Gy, and a z-axis gradient magnetic field Gz.

The gradient magnetic field generation means 130 includes x-axis gradient magnetic field generation means 133 having z-axis magnetic field magnitude (dBz/dx=Gx) varying along x-axis, y-gradient magnetic field generation means 135 having z-axis magnetic field magnitude (dBz/dy=Gy) varying along y-axis and z-axis gradient magnetic field generation means 131 having z-axis magnetic field magnitude (dBz/dz=Gz) varying along z-axis.

The z-axis gradient magnetic field generation means 131 may be a pair of Helmholtz coils spaced apart from each other in z-axis direction. The x-axis gradient magnetic field generation means 133 includes a pair of square coils and spaced apart from each other in a positive z-axis region in the x-axis direction and a pair of square coils spaced apart from each other in a negative z-axis region in the x-axis direction. Each of the coils may be disposed in each quadrant in an xz plane, and a normal vector of a plane in which each of the coils is disposed may be diagonal in the xz plane. The y-axis gradient magnetic field generation means 135 may include four coils each being disposed in each quadrant in a yz plane, and the normal vector of a plane in which each of the coils is disposed may be diagonal in the yz plane.

The magnetic field measurement means 160 is disposed adjacent to the measurement target 170 and acquires a magnetic resonance signal emitted from the measurement target 170. The magnetic field measurement means 160 may measure a magnetic flux in the y-axis direction of the measurement target 170. An output signal of the magnetic field measurement means 160 is provided to a measurement and analysis unit 180. The magnetic field measuring means 160 may measure a resonated magnetization component of the measurement target 170.

The magnetic field measurement means 160 includes a flux transformer 161 configured to detect and/or attenuate/amplify a flux, a superconducting quantum interference device (SQUID) 163 configured to receive an output signal of the flux transformer 161 and detect a magnetic field to convert the magnetic field into a voltage signal, and a Dewar 165 configured to store a coolant.

The SQUID 163 is a type of transducer that converts a variation of an external flux into a voltage by combination of the Josephson effect and the magnetic flux quantization effect that only superconductors exhibit. The SQUID 163 is a magnetic sensor in which one or two Josephson junctions are inserted into one superconducting loop. An RF SQUID may be a SQUID in which one Josephson junction is inserted into one superconducting loop. A DC SQUID may be a SQUID in which two Josephson junctions are inserted into one superconducting loop. The RF SQUID operates in a manner of outputting an AC voltage in an RF frequency band and varying its frequency depending on an applied flux. The DC SQUID operates in a manner of generating a DC voltage as a function of an applied flux, and the function is given to vibrate in cycles of $\Phi 0$ (=2.07×10-15 Wb) which is a quantum value of the applied flux. The detailed form of the flux/voltage conversion function may be determined depending on detailed structures of the DC SQUID.

The flux transformer 161 may include a pick-up coil configured to detect a flux and transform the detected flux into a superconducting current and/or an input coil configured to amplify or attenuate the superconducting current in a form of a flux in the SQUID 163. The flux transformer 161 may be formed of a superconductor. The pick-up coil may have a large area to detect a large amount of flux. The input coil may have an area similar to an area of the SQUID 163 to focus on the SQUID 163 and may be wound many times to change an amplification factor or an attenuation factor.

The flux transformer 161 may include a gradiometer including one or more loop pairs in which pick-up coils are wound in opposite directions.

The SQUID 163 may be connected to an FLL unit 188 through a conducting wire. The flux transformer 161 may measure a flux in the y-axis direction.

A SQUID need to be protected to stably operate under a strong magnetic field such as a pre-polarizing magnetic field Bp. Therefore, an ultra-low field MRI system uses a superconducting shield to protect a SQUID. However, the SQUID cannot function as a magnetic field sensor when the entire SQUID sensor is superconductively shielded. For this reason, when shielding is performed using a superconductor, only a SQUID portion and an input coil portion of a flux transformer are superconductively shielded and the flux transformer is disposed outside the superconducting shield. In this case, the SQUID itself is protected from a strong magnetic field due to the superconducting shield 164 but a current inducted from the flux transformer 161 cannot be prevented from applying to the SQUID. Thus, a current restriction unit 162 is disposed in the ultra-low field NMR system to prevent an overcurrent induced from the readout coil from applying to the SQUID.

The measurement and analysis unit 180 includes a flux locked loop (FLL) unit 188 configured to linearize the voltage signal of the SQUID 163 and provide the linearized voltage signal as a voltage signal proportional to a detected magnetic field, a sensor signal processor 186 configured to process the voltage signal to remove noise and amplify the processed signal, and a sensor controller 187 configured to provide a control signal to the FLL unit 188.

The FLL unit 188 may include an input terminal configured to receive the output signal of the SQUID 163, an integrator, a feedback-type linearization circuit, a feedback coil, and the like. The FLL unit 188 may convert variation of a flux into a voltage signal having a much wider range than a flux quantum value $\Phi_0$ and may output the converted voltage signal.

The pulse sequence generator 122 receives a control signal of the controller 185 to provide a pulse sequence to a pre-polarization coil driver 152, a measurement bias magnetic field driver 142, and gradient magnetic field drivers 132a and 132b.

A magnetic field controller 101 may apply various magnetic fields to the measurement target 170 in synchronization with the measurement and analysis unit 180. The magnetic field controller 101 may control the pre-polarization generation means 150, the measurement bias magnetic field generation means 140, and the gradient magnetic field generation means 130 according to a series of order.

The magnetic field controller 101 includes the pre-polarization coil driver 152 configured to intermittently apply a current to the pre-polarizing magnetic field generation means 150 to generate a pre-polarizing magnetic field Bp. The pre-polarizing magnetic field generation means 150 is connected to the pre-polarization coil driver 152. The pre-polarization coil driver 152 is connected to a pre-polarizing magnetic field power supply 154.

The measurement bias magnetic field generation means 140 configured to apply a measurement bias magnetic field Bm to the measurement target 170 is connected to the measurement bias magnetic field driver 142. The measurement bias magnetic field driver 142 is connected to the measurement bias magnetic field power supply 144.

The gradient magnetic field generation means 130 is connected to the gradient magnetic field driver 132b, and the gradient magnetic field driver 132b is connected to a gradient magnetic field power supply 134. The gradient magnetic field power supply 134 is connected to a gradient magnetic field driver 132a.

The measurement and analysis means 180 may process a magnetic resonance signal (FID signal or gradient echo signal) to extract a nuclear magnetic resonance image.

The gradient magnetic field generation means 130 may apply gradient magnetic fields Gx, Gy, and Gz to the measurement target 170. The gradient magnetic field power supply 134 supplies a current to the gradient magnetic field generation means 130 to apply the gradient magnetic fields Gx, Gy, and Gz to the measurement target 170. The gradient magnetic field driver 132b may adjust the current applied to the gradient magnetic field generation means 130 to intermittently generate the gradient magnetic fields Gx, Gy, and Gz. The gradient magnetic field driver 132a may adjust an intensity of the current applied to the gradient magnetic field generation means 130 to generate the gradient magnetic fields Gx, Gy, and Gz. The gradient magnetic field generation means 130 may generate the gradient magnetic fields Gx, Gy, and Gz.

The measurement bias magnetic field generation means 140 may generate a spatially uniform and low measurement bias magnetic field Bm. The measurement bias magnetic field generation means 140 may be connected to the measurement bias magnetic field power supply 144. The measurement bias magnetic field driver 142 may intermittently adjust the current applied to the measurement bias magnetic field generation means 140 to generate the measurement bias magnetic field Bm.

The pulse sequence generator 122 may generate a pulse sequence and supply the pulse sequence to the pre-polarization coil driver 152, the measurement bias magnetic field driver 142, and the gradient magnetic field drivers 132a and 132b to obtain a FID signal or a gradient echo signal.

The controller 185 may process a signal of the sensor signal processor 186 and may control the pulse sequence generator 122 and the sensor controller 187.

According to an example embodiment, the measurement target 170 may be an MREIT phantom. The MREIT phantom was used to acquire a nuclear magnetic resonance signal instead of a part of the human body. The MREIT phantom has a shape of a cylinder extending in the z-axis direction and is filled with a saline solution. Electrodes are disposed at opposite ends of the MREIT phantom in such a manner that a current may flow in the z-axis direction. The MREIT phantom is configured in such a manner that an alternating current flows in the z-axis direction with a vibration frequency $f_{MOD}$ by an AC power supply. Accordingly, the modulated magnetic field $B_{MOD}$ is generated in an azimuthal direction of a cylindrical coordinate system with a vibration frequency.

The pre-polarizing magnetic field Bp and the measurement bias magnetic field Bm are parallel to each other and are applied in the z-axis direction. The modulated magnetic field $B_{MOD}$ is generated perpendicular to the direction of the measurement bias magnetic field Bm when an alternating current flows to the saline solution inside the MREIT phantom in parallel with the direction of the measurement bias magnetic field Bm.

Accordingly, an NMR signal is absent when the modulated magnetic field $B_{MOD}$ is absent, but is generated when the modulated magnetic field $B_{MOD}$ is generated.

At this point, when a vibration frequency of the modulated magnetic field or the alternating current is made to match a resonance frequency of a proton produced by the measurement bias magnetic field Bm, a proton of a peripheral saline solution cause a resonance with the modulated magnetic field to generate an NMR signal.

Magnitudes of a pre-polarizing magnetic field Bp and a measurement bias magnetic field Bm used in an experiment were about 50 µT and about 34.57 µT, respectively. A vibration frequency of a modulated magnetic field $B_{MOD}$ was 1472 Hz that was a nuclear magnetic resonance frequency corresponding to the measurement bias magnetic field Bm using an arbitrary function generator, and an applied voltage of the function generator was 10 Vpp. To obtain the maximum nuclear magnetic resonance signal, the nuclear magnetic resonance signal was obtained while fixing the magnitude of the modulating magnetic field $B_{MOD}$ and changing an application time $t_{MOD}$ of the modulated magnetic field $B_{MOD}$.

Referring to FIG. 6, the nuclear magnetic resonance signals were averaged five times at each application time $t_{MOD}$ of the modulated magnetic field. As a result, the maximum NMR signal was obtained when the application time $t_{MOD}$ of the modulated magnetic field was 39.4 ms.

Under the above condition, an imaging experiment was performed using a pulse sequence. In an MREIT imaging experiment, a two-dimensional gradient-echo pulse sequence in FIG. 5 was used. More specifically, the two-dimensional gradient-echo pulse sequence includes the steps of applying a pre-polarizing magnetic field applied for an application time $t_{Bp}$ of a pre-polarizing magnetic field Bp, applying a modulating magnetic field $B_{MOD}$ for an application time $t_{MOD}$ of the modulated magnetic field $B_{MOD}$, applying gradient magnetic fields Gx and Gz for an application time $t_{pw}$, measuring a nuclear magnetic resonance signal (NMR signal) for a predetermined measurement time $t_{measurement}$, and providing a repetition time $t_{repetition}$ to remove all the magnetic fields for repetition.

The pre-polarizing magnetic field Bp is applied in the form of a pulse to pre-polarize the measurement target to magnetize the measurement target in a direction of the pre-polarizing magnetic field.

In the operation of applying the modulated magnetic field $B_{MOD}$, the measurement bias magnetic field Bm is applied to the measurement target and the modulated magnetic field $B_{MOD}$ is applied in the form of a pulse for the application time $t_{MOD}$. Thus, a proton of the measurement target performs nuclear magnetic resonance under the measurement bias magnetic field by the modulated magnetic field $B_{MOD}$. A pulse application time of the modulated magnetic field may be set to the application time $t_{MOD}$ to obtain a maximum nuclear magnetic resonance signal.

Then, gradient magnetic fields Gx and Gz are applied. The gradient magnetic fields Gx and Gz may include an x-axis gradient magnetic field Gx and a z-axis gradient magnetic field Gz.

Parameters used in the experiment are an application time $t_{Bp}$ of the pre-polarizing magnetic field that is 1 second (sec), an application time $t_{MOD}$ of the modulated magnetic field that is 39.4 milliseconds (msec), an application time $t_{pw}$ of the gradient magnetic field is 0.2 sec, a measurement time $t_{measurement}$ of the nuclear magnetic resonance signal that is 2 sec, and the repetition time $t_{Repetition}$ that is 25 sec.

Thirty one (31) steps for phase encoding were given. A magnitude difference ΔGz of the z-axis gradient magnetic field Gz in the respective steps for phase encoding was 0.014 µT/cm and the magnitude of the x-axis gradient magnetic field Gx for frequency encoding was 0.13 µT/cm.

Referring to FIG. 6, the obtained MREIT magnetic resonance image indicates a cylindrical MREIT current phantom image. Thus, an ultra-low field MM-based MRIIT image may be obtained.

Figure 8:
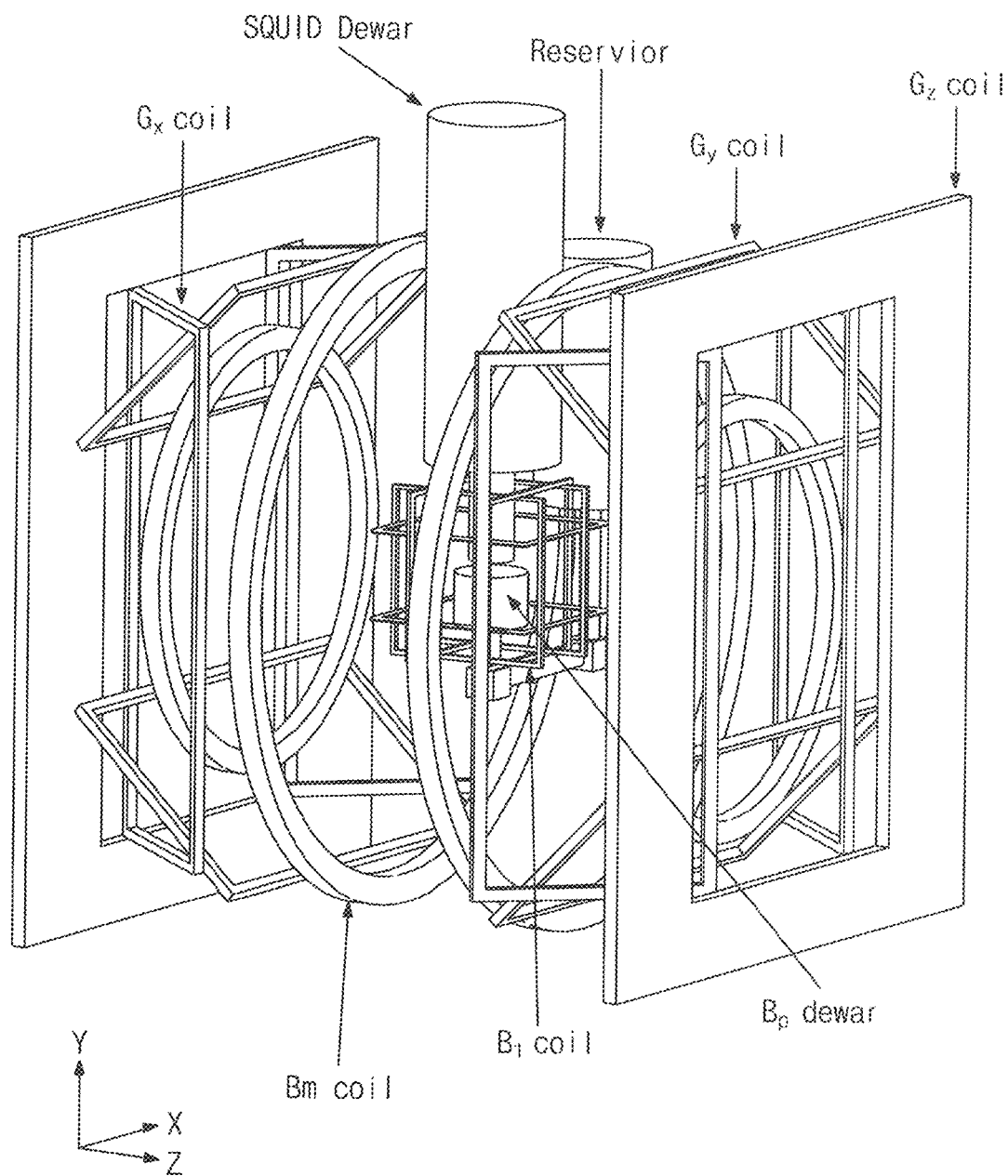
FIG. 8 is a perspective view of a coil structure of an ultra-low field nuclear magnetic resonance device according to another example embodiment of the present disclosure.

FIG. 8 is a perspective view of a coil structure of an ultra-low field nuclear magnetic resonance device according to another example embodiment of the present disclosure.

Figure 9:
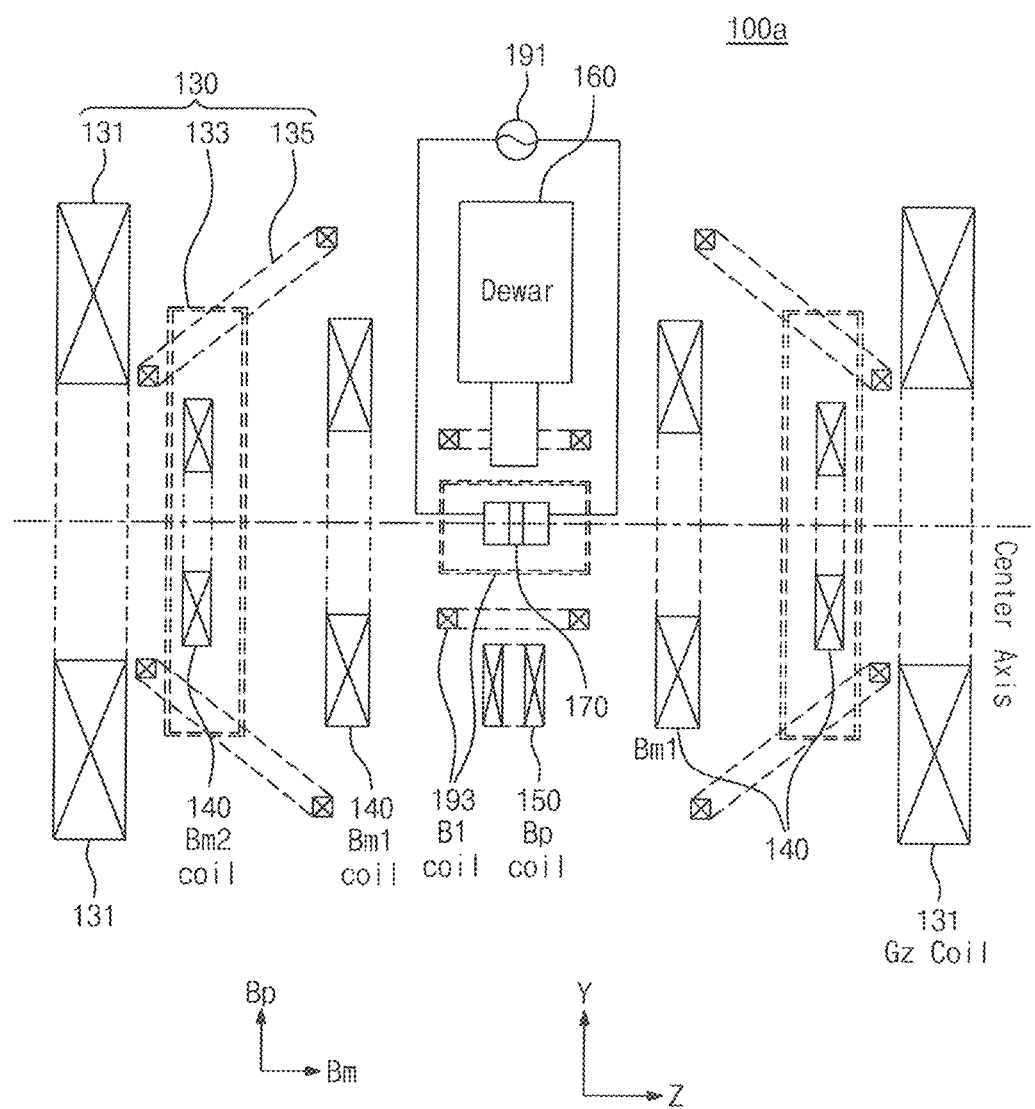
FIG. 9 is a conceptual diagram of the coil structure of the ultra-low field nuclear magnetic resonance device in FIG. 8.

FIG. 9 is a conceptual diagram of the coil structure of the ultra-low field nuclear magnetic resonance device in FIG. 8.

Figure 10:
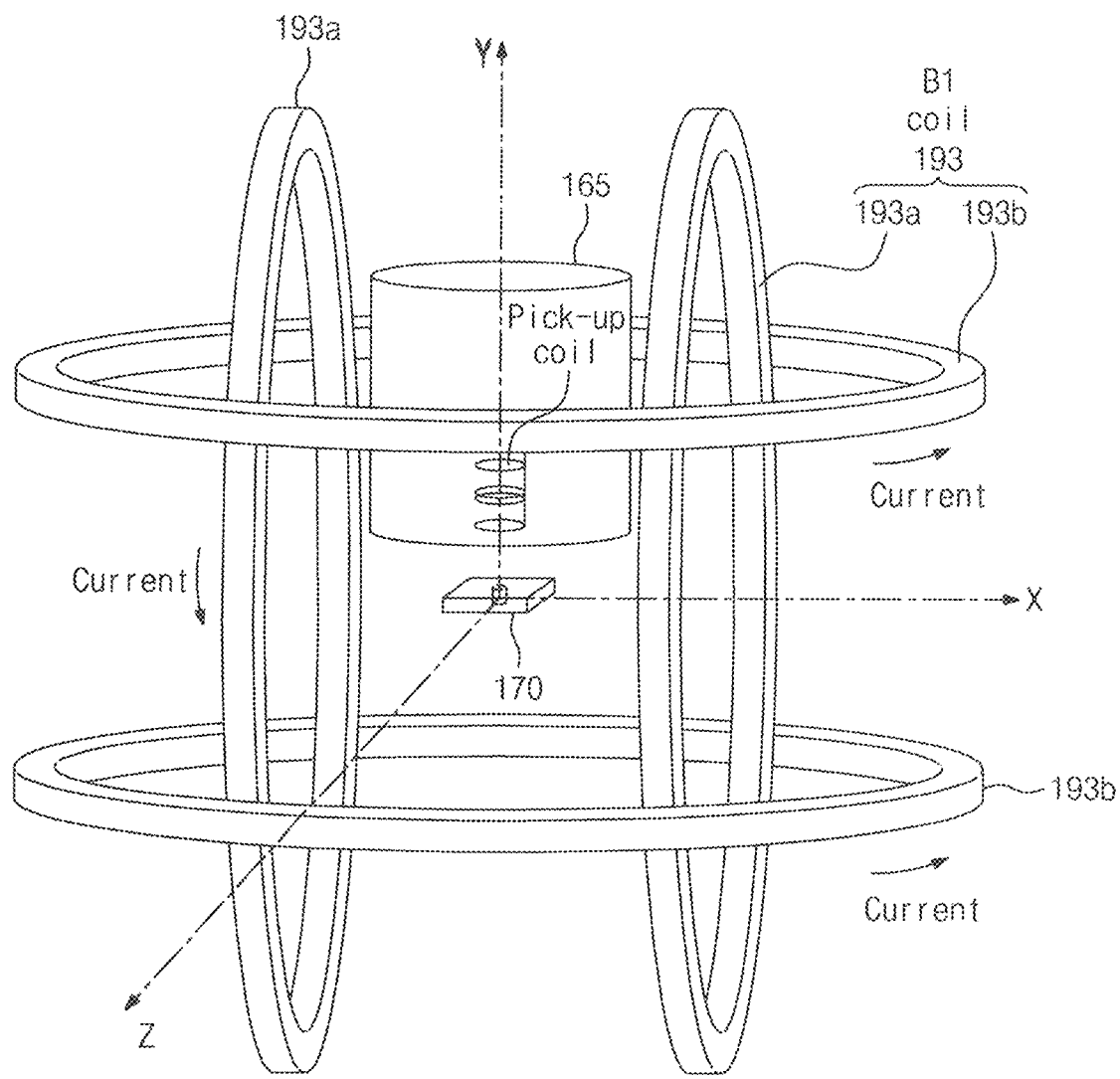
FIG. 10 is a perspective view of an excitation field coil of the ultra-low field nuclear magnetic resonance device in FIG. 8.

FIG. 10 is a perspective view of an excitation field coil of the ultra-low field nuclear magnetic resonance device in FIG. 8.

Figure 11:
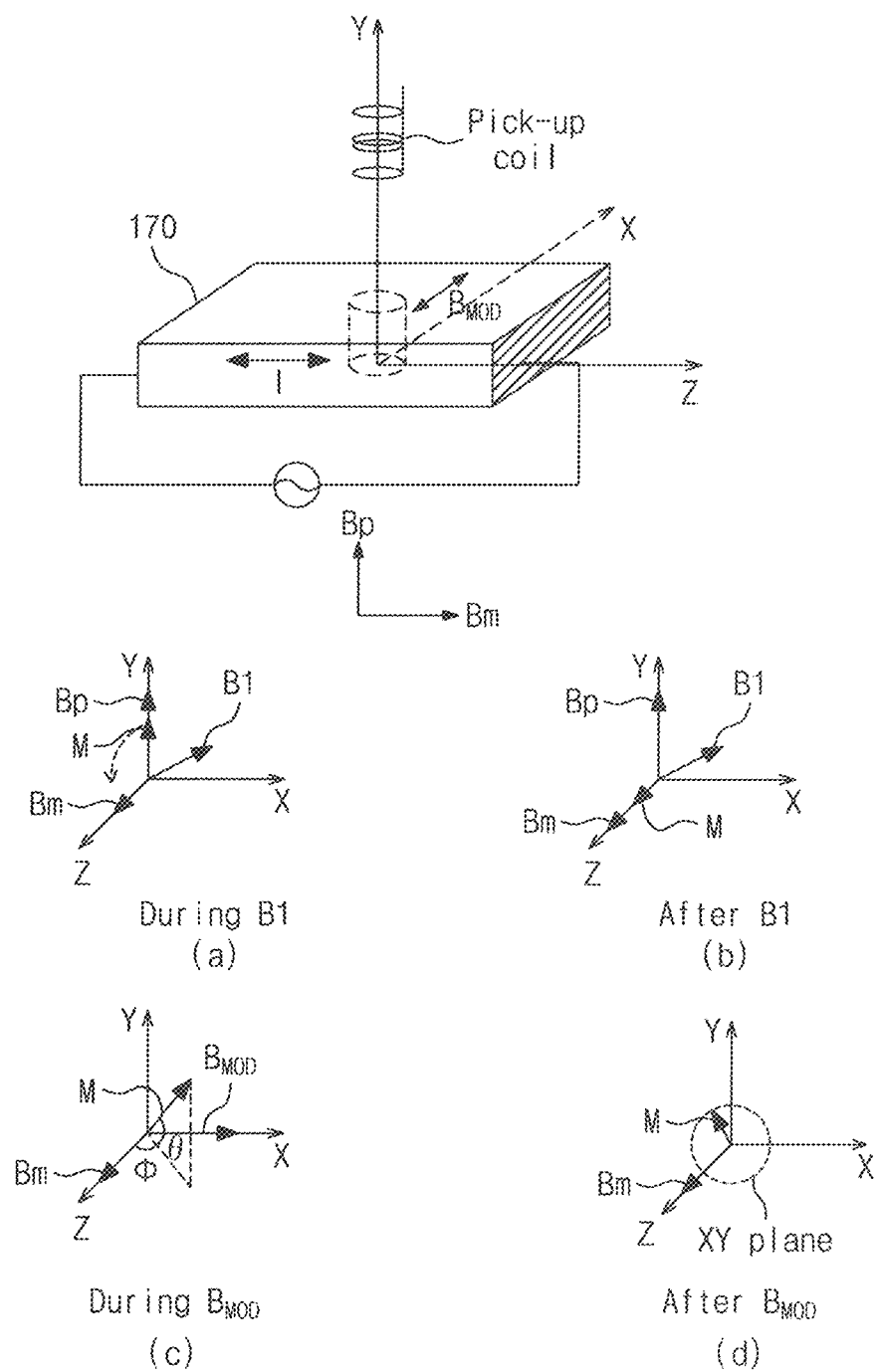
FIG. 11 illustrates a phantom as a measurement target and a magnetic field direction of the ultra-low field nuclear magnetic resonance device in FIG. 8.

FIG. 11 illustrates a phantom as a measurement target and a magnetic field direction of the ultra-low field nuclear magnetic resonance device in FIG. 8.

Figure 12:
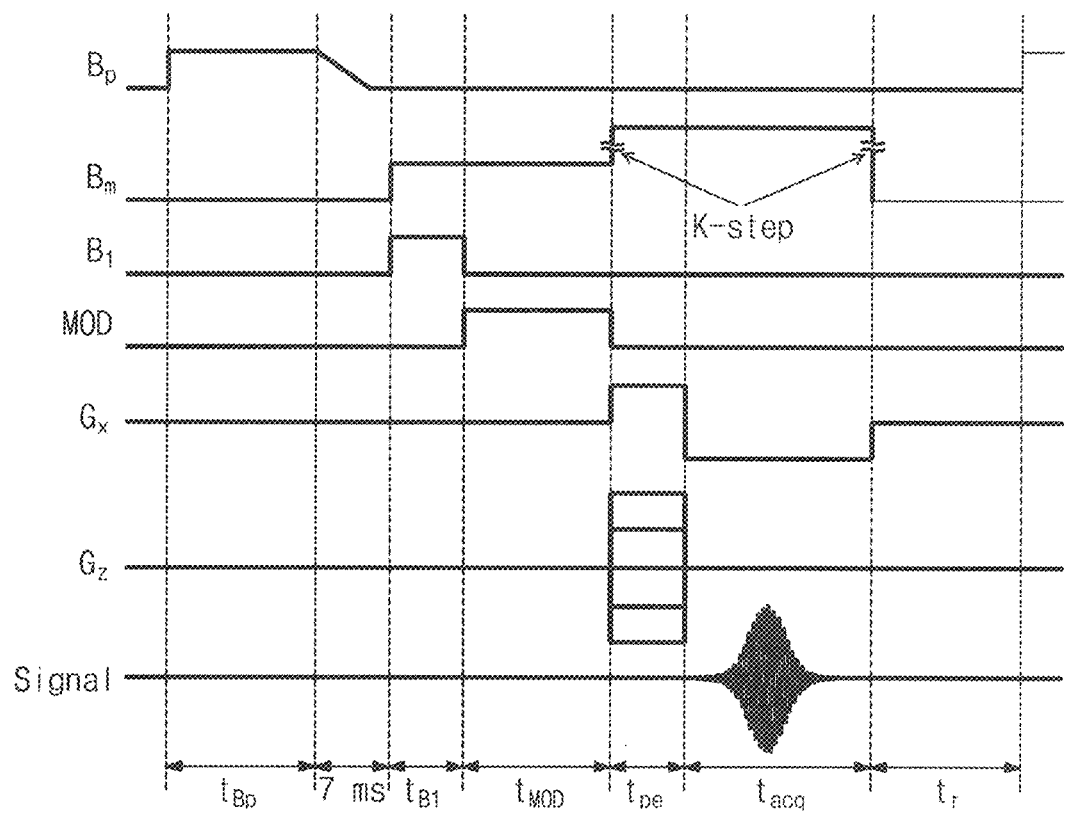
FIG. 12 is a timing chart illustrating a pulse sequence of the ultra-low field nuclear magnetic resonance device in FIG. 8.

FIG. 12 is a timing chart illustrating a pulse sequence of the ultra-low field nuclear magnetic resonance device in FIG. 8.

Referring to FIGS. 8 to 16, an ultra-low field nuclear magnetic resonance device 100a includes an AC power supply 191 configured to supply a current to a measurement target such that a current flows to the measurement target, a magnetic field measurement means 160 disposed close to the measurement target, and a measurement bias magnetic field generation means 140 configured to apply a measurement bias magnetic field corresponding to a proton magnetic resonance frequency of the measurement target. A vibration frequency of the AC power supply 191 matches a proton magnetic resonance frequency of the measurement target, and the magnetic field measurement means 160 measures a nuclear magnetic resonance signal generated from the measurement target.

The pre-polarizing magnetic field generation means 150 generates a pre-polarizing magnetic field Bp to pre-polarize the measurement target. An excitation magnetic field generation means 193 generates a circularly polarized excitation magnetic field B1 to switch a magnetization direction of the measurement target into a direction of the measurement bias magnetic field Bm. A direction of the pre-polarizing magnetic field Bp is perpendicular to the direction of the measurement bias magnetic field Bm and the circularly polarized excitation field B1 rotates the magnetization direction in the direction of the measurement bias magnetic field Bm. The circularly polarized excitation field may be transformed to a linearly polarized excitation field. More specifically, when the magnitude of an excitation magnetic field is similar to or greater than the magnitude of a measurement bias magnetic field, a circularly polarized excitation magnetic field may be used. Meanwhile, when the magnitude of the excitation magnetic field is smaller than the magnitude of the measurement bias magnetic field, a linearly polarized excitation magnetic field may be used.

Referring to FIG. 11, an MREIT phantom includes a hexahedron having a size of 50×150×20 mm³ and a cylindrical agarose gel provided at its center to have a diameter of about 20 mm. A concentration of the cylindrical agarose gel was 1 percent (%) (0.9% saline solution was used), and the remaining space of the hexahedron was filled with 0.9% saline solution. Since organs of the human body have different electrical conductivities, a phantom including two parts having different electrical conductivities was fabricated to simulate the organs.

A liquid helium Dewar 165 stores a SQUID sensor, and the pre-polarizing magnetic field generation means 150 is a pancake-type coil cooled with nitrogen. The measurement bias magnetic field generation means 140 is a double Helmholtz coil. The gradient magnetic field generation means 130 may be a triaxial gradient magnetic field coil.

When the pre-polarizing coil or the pre-polarizing magnetic field generation means 150 is a solenoid coil, the degree of freedom in phantom fabrication is reduced. Accordingly, the pre-polarizing coil is a pancake coil configured to generate a magnetic field in the y-axis direction. In this case, the pre-polarizing magnetic field Bp is in the y-axis direction and the measurement bias magnetic field Bm is in the z-axis direction, i.e., the pre-polarizing magnetic field and the measurement bias magnetic field are perpendicular to each other. Accordingly, there is difficulty in observing a resonance phenomenon caused by the modulated magnetic field $B_{MOD}$. Therefore, magnetization M aligned by the pre-polarizing magnetic field Bp needs to rotate in the direction of the measurement bias magnetic field Bm. Therefore, the excitation magnetic field generating means 193 may generate an excitation magnetic field B1 having an x-axis component and a y-axis component, and the excitation magnetic field B1 may provide a torque such that the magnetization M is directed toward the measurement bias magnetic field Bm. The excitation magnetic field generation means 193 includes a first excitation magnetic field generating means 193a including a Helmholtz coil configured to provide an x-axis magnetic field component and a second excitation magnetic field generation means 193b including a Helmholtz coil configured to provide a y-axis magnetic field component.

In addition, a modulated magnetic field $B_{MOD}$ perpendicular to the direction of the measurement bias magnetic field Bm is applied. The magnetization rotated by the excitation field is subjected to torque by the modulated magnetic field $B_{MOD}$, and then the magnetization rotated by the modulated magnetic field $B_{MOD}$ is rotated in a plane perpendicular to the measurement bias magnetic field Bm. For this reason, an NMR signal may not be generated in the absence of the modulated magnetic field $B_{MOD}$. However, an NMR signal is generated when the modulated magnetic field $B_{MOD}$ is applied. In this case, a vibration frequency of the modulated magnetic field $B_{MOD}$ is set to be the same as a resonance frequency of a proton produced by the measurement bias magnetic field Bm. The modulated magnetic field $B_{MOD}$ causes nuclear magnetic resonance with a proton of the saline solution, and a nuclear magnetic resonance signal is generated.

Magnitudes of the pre-polarizing magnetic field Bp and the measurement bias magnetic field Bm used in the present embodiment are about 92.5 mT (when measured on a top plate of the Dewar) and 4.86 µT, respectively. The AC power supply includes arbitrary function generator, and a vibration frequency of the function generator is 207 Hz that is the same as the resonance frequency of the measurement bias magnetic field Bm (Bm=4.86 µT).

Referring to FIG. 12, an MREIT imaging pulse sequence is a two-dimensional gradient-echo pulse sequence. The MREIT imaging pulse sequence includes the steps of applying a pre-polarizing magnetic field Bp for an application time $t_{Bp}$ of a pre-polarizing magnetic field Bp, providing a delay time (td=7 msec), applying an excitation magnetic field B1 and applying a measurement bias magnetic field Bm for an application time $t_{B1}$ of the excitation magnetic field B1, applying a modulated magnetic field $B_{MOD}$ for an application time $t_{MOD}$ of a modulated magnetic field $B_{MOD}$, applying gradient magnetic fields Gx and Gz while increasing the magnitude of the measurement bias magnetic field Bm, measuring the nuclear magnetic resonance signal for a predetermined time $t_{acq}$, and providing a repetition time $t_r$.

A pre-polarizing magnetic field applying means 150 applies a pre-polarizing magnetic field to the measurement target in the y-axis direction. Thus, magnetization M of the measurement target is aligned in the direction of the pre-polarizing magnetic field Bp.

A time delay of 7 ms is provided after the pre-polarizing magnetic field Bp is turned off.

The measurement bias magnetic field Bm is applied such that the magnetization M is directed toward the pre-polarizing magnetic field Bp as much as possible without being affected by the measurement bias magnetic field Bm.

The excitation magnetic field B1 is applied. The excitation magnetic field is a circularly polarized pulse and includes an x-axis component and a y-axis component. The excitation field B1 allows magnetization to be directed in the direction of the measurement bias magnetic field Bm. A frequency of the excitation magnetic field B1 may be the same as a proton resonance frequency. The excitation magnetic field B1 may be transformed into a linearly polarized excitation magnetic field. More specifically, a circularly polarized excitation magnetic field may be used when the magnitude of the excitation magnetic field is similar to or greater than the magnitude of the measurement bias field Bm. On the other hand, a linearly polarized excitation magnetic field may be used when the magnitude of the excitation magnetic field is smaller than the magnitude of the measurement bias magnetic field Bm.

Then, the modulated magnetic field $B_{MOD}$ is applied. As the modulated magnetic field $B_{MOD}$ is applied for an application time $t_{MOD}$ of the modulated magnetic field $B_{MOD}$, the modulated magnetic field $B_{MOD}$ causes the magnetization to be twisted at a certain angle from the direction of the measurement bias magnetic field Bm.

A K-step is used to increase the measurement bias magnetic field Bm. The magnitude of the measurement bias magnetic field Bm increases from 4.86 µT to 34.5 µT, and two-dimensional gradient magnetic fields Gx and Gz are applied. Thus, an NMR signal is observed.

The K-step means that the magnitude of the measurement bias magnetic field Bm increases in a stepped fashion. In ultra-low field NMR, the K-step has various advantages. Since a signal linewidth of NMR is basically very narrow in ultra-low field NMR, a measurement bandwidth is very narrow. Due to the degree of freedom in selecting a measurement frequency of the K-step, SNR may be increased by measuring a signal in a region in which a system noise is small, which is a great advantage, in particular, in an MRI experiment to eliminate interference from the power noise generated by many gradient magnetic field coils and a power system. In addition, a gradient magnetic field should be applied to obtain an image. The amplitude of the gradient magnetic field is in proportion to a spatial resolution of the image. However, when an NMR signal itself is in the range of several tens of hertz (Hz), the magnitude of an available image gradient magnetic field and an available image acquisition space may be limited. A K-step technique may visualize with a sufficiently high intensity of the image gradient magnetic field by moving the measurement frequency to a sufficiently high frequency and relatively reduce the influence of the concomitant gradient.

Figure 13:
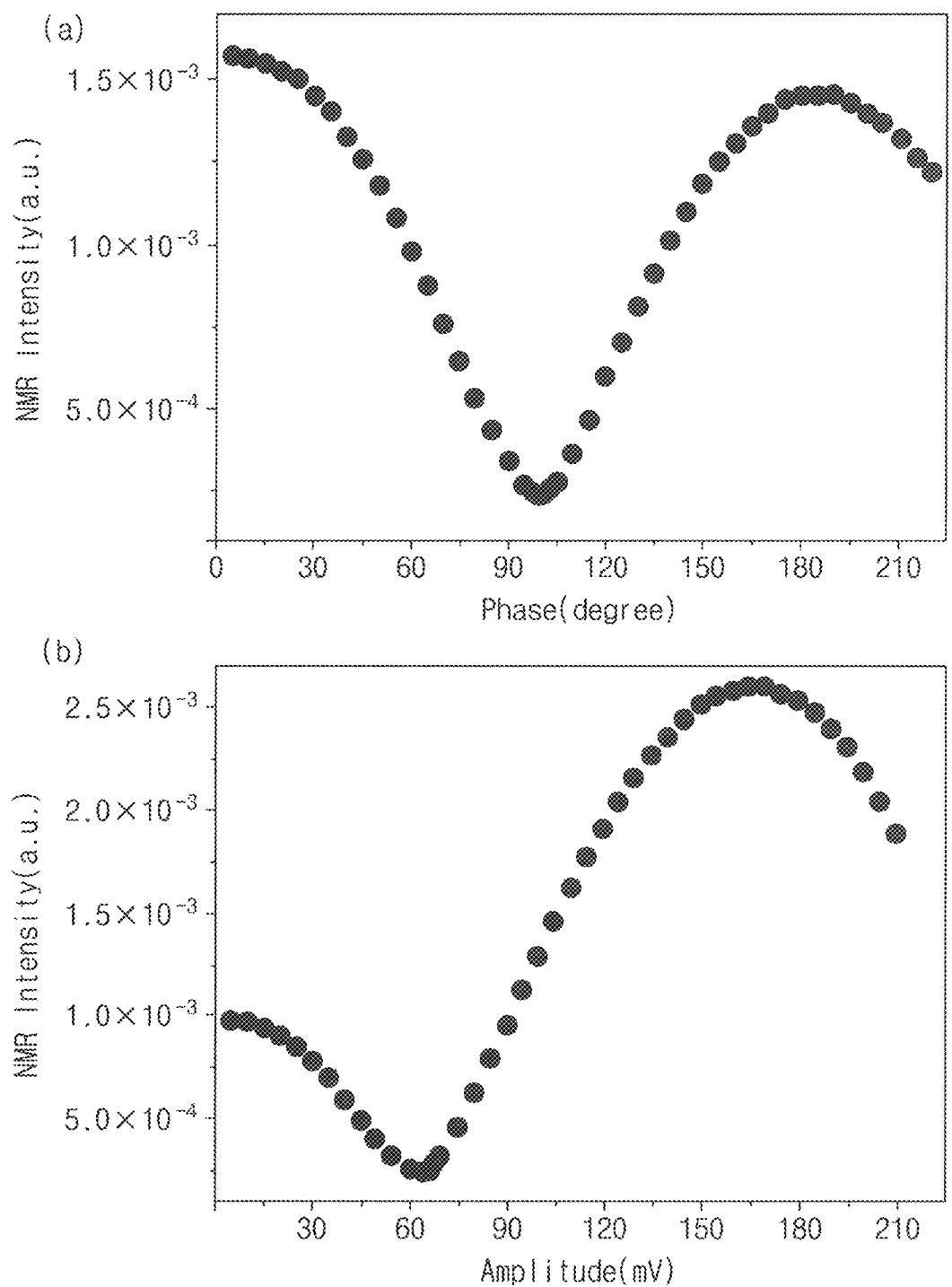
FIG. 13 illustrates the intensity of a nuclear magnetic resonance signal depending on a phase (a) and an amplitude (b) generating a circularly polarized excitation magnetic field.

FIG. 13 illustrates the intensity of a nuclear magnetic resonance signal depending on a phase (a) and an amplitude (b) generating a circularly polarized excitation magnetic field.

Referring to FIGS. 10 and 13, to determine parameters of a circularly polarized excitation magnetic field B1 that directs a direction of magnetization M toward a direction of a measurement bias magnetic field, an applied time $t_{B1}$ of the excitation magnetic field was fixed (fixed to 1 ms) and an NMR signal was measured for a measurement time $t_{acq}$ of the NMR signal in a two-dimensional gradient-echo pulse sequence (except for an applied portion $t_{MOD}$ of a modulated magnetic field and an applied portion $t_{pe}$ of a gradient magnetic field, K-step was not used). The parameters used were as follows: an application time $t_{Bp}$ of the pre-polarizing magnetic field was 1 second, the application time $t_{B1}$ of the excitation magnetic field was 1 msec, the measurement time $t_{acq}$ of the NMR signal was 2 seconds, and a repetition time $t_r$ was 3 seconds. The NMR signals were measured 4 times at each point and averaged. An arbitrary function generator (AFG) was used as a current source of the circularly polarized excitation field. A phase and an amplitude of the arbitrary function generator were adjusted to search a point in which the NMR signal is minimized, i.e., a condition of the circularly polarized excitation magnetic field in which magnetization was maximally directed to the measurement bias magnetic field. As a result, the amplitude and the phase of the arbitrary function generator were 63 mV and 99 degrees, respectively. For this reason, when a 207 Hz sine function was applied for 1 ms that was the excitation time $t_{B1}$ of the excitation magnetic field, it was predicted that the magnetization is directed toward the measurement bias magnetic field.

Figure 14:
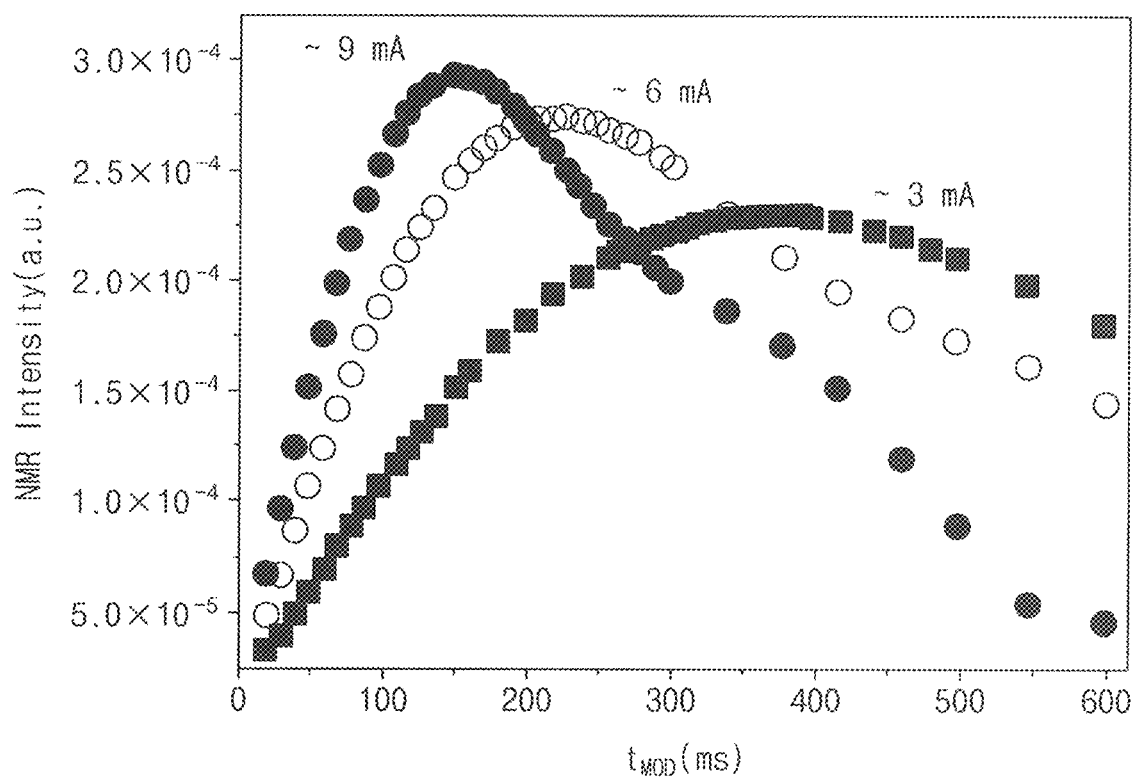
FIG. 14 illustrates the intensity of a nuclear magnetic resonance signal depending on an application time of a modulated magnetic field and the intensity of an alternating current.

FIG. 14 illustrates the intensity of a nuclear magnetic resonance signal depending on an application time of a modulated magnetic field and the intensity of an alternating current.

Referring to FIG. 14, a modulated magnetic field (the intensity of an alternating current) was fixed and an application time $t_{MOD}$ of the modulated magnetic field, in which a nuclear magnetic resonance signal is maximized, was measured. A two-dimensional gradient-echo pulse sequence (except for an applied portion tpe of the gradient magnetic field) was used to measure. That is, after the application time $t_{MOD}$ of the modulated magnetic field, the magnitude of the measurement bias magnetic field was increased from 4.86 µT to 34.5 µT using the K-step and the NMR signal was measured. Parameters used in the experiment were as follows: an application time $t_{Bp}$ of a pre-polarizing magnetic field was 1 second, an application time $t_{B1}$ of an excitation magnetic field was 1 msec, a measurement time $t_{acq}$ of an NMR signal was 2 seconds, a repetition time $t_r$ of the NMR signal was 3 seconds. In addition, a vibration frequency $f_{MOD}$ of the modulated magnetic field was 207 Hz. The NMR signals were measured four times at each application time $t_{MOD}$ of the modulated magnetic field and averaged.

Referring to FIG. 14, when an AC current of about 9 mA is applied to the MREIT phantom for about 150 ms (the application time $t_{MOD}$ of the modulated magnetic field), a maximum NMR signal was observed and it could be confirmed that the NMR signal decreased again after 150 ms. As the magnitude of the modulated magnetic field is reduced by reducing the alternating current, a required application time is increased. From the above result, we could know that the spins around a current source resonate well with a vibration frequency of an externally applied modulated magnetic field.

Figure 15:
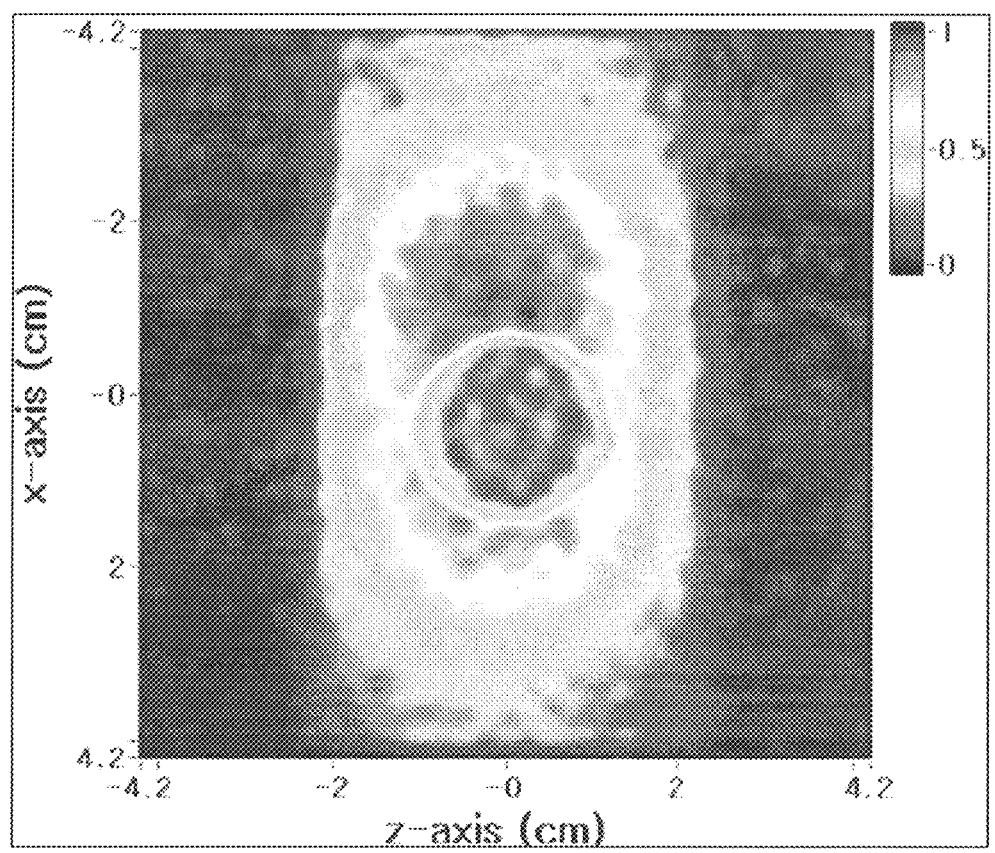
FIG. 15 is a proton density magnetic resonance image of an MREIT phantom according to an example embodiment of the present disclosure.

FIG. 15 is a proton density magnetic resonance image of an MREIT phantom according to an example embodiment of the present disclosure.

Referring to FIG. 15, a two-dimensional gradient-echo pulse sequence (except for an applied portion of a circularly polarized excitation magnetic field and an applied portion of a modulated magnetic field) was used to confirm whether a measurement target (phantom) was properly imaged. Accordingly, a measurement bias magnetic field of 34.5 μT and a biaxial gradient magnetic field were applied with a delayed time of 7 ms without K-step. Parameters used in the experiment were as follows: an application time $t_{Bp}$ of a pre-polarizing magnetic field was 1 second, an application time $t_{pe}$ of a gradient magnetic field was 0.1 sec, a measurement time $t_{acq}$ was 0.3 second, and a repetition time $t_r$ was 4.7 seconds. Forty one (41) steps were given for phase encoding. A magnitude difference ΔGz of a z-axis gradient magnetic field Gz for providing phase encoding in each of the steps was 0.028 μT/cm, an x-axis gradient magnetic field Gx was 0.56 μT/cm, and they were averaged 16 times.

Thus, it was confirmed that the MREIT phantom was properly imaged. A center circle is a portion with 1% agarose gel.

Figure 16:
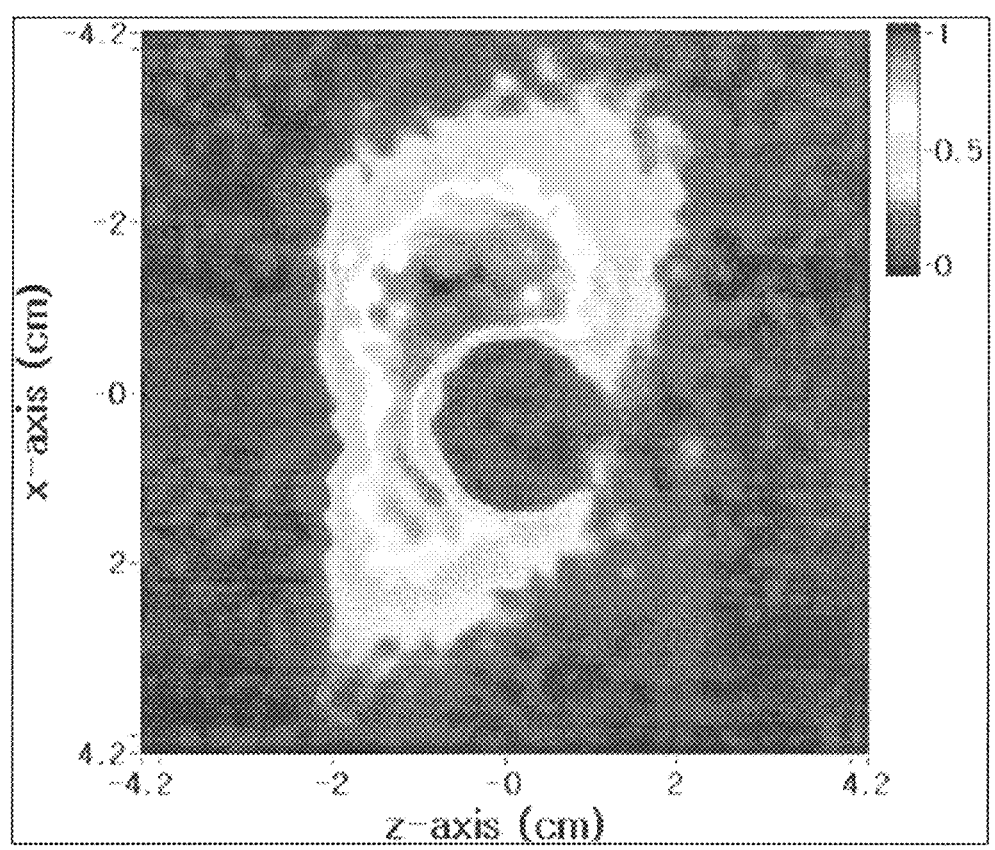
FIG. 16 is a magnetic resonance image formed by an alternating current (modulated magnetic field) of an MREIT phantom according to an example embodiment of the present disclosure.

FIG. 16 is a magnetic resonance image formed by an alternating current (modulated magnetic field) of an MREIT phantom according to an example embodiment of the present disclosure.

Referring to FIG. 16, when a modulated magnetic field $B_{MOD}$ was applied, an MREIT image was acquired. A two-dimensional gradient-echo pulse sequence was used. Parameters used in the experiment were as follows: an application time $t_{Bp}$ of a pre-polarizing field was 1 second, an application time $t_{B1}$ of an excitation magnetic field was 1 msec, an application time $t_{MOD}$ of the modulated magnetic field was 149.75 msec, a measurement time $t_{acq}$ of an NMR signal was 0.3 second, a repetition time $t_r$ was 4.7 seconds, the intensity of an alternating current was 9 mA, and a vibration frequency of the alternating current was 207 Hz. Forty one (41) steps were given for phase encoding. A magnitude difference ΔGz of a z-axis gradient magnetic field Gz for providing phase encoding in each of the steps was 0.028 μT/cm, an x-axis gradient magnetic field Gx was 0.56 μT/cm, and they were averaged 16 times. As the alternating current was applied, the modulated magnetic field was generated and the resulting image appeared.

Figure 17:
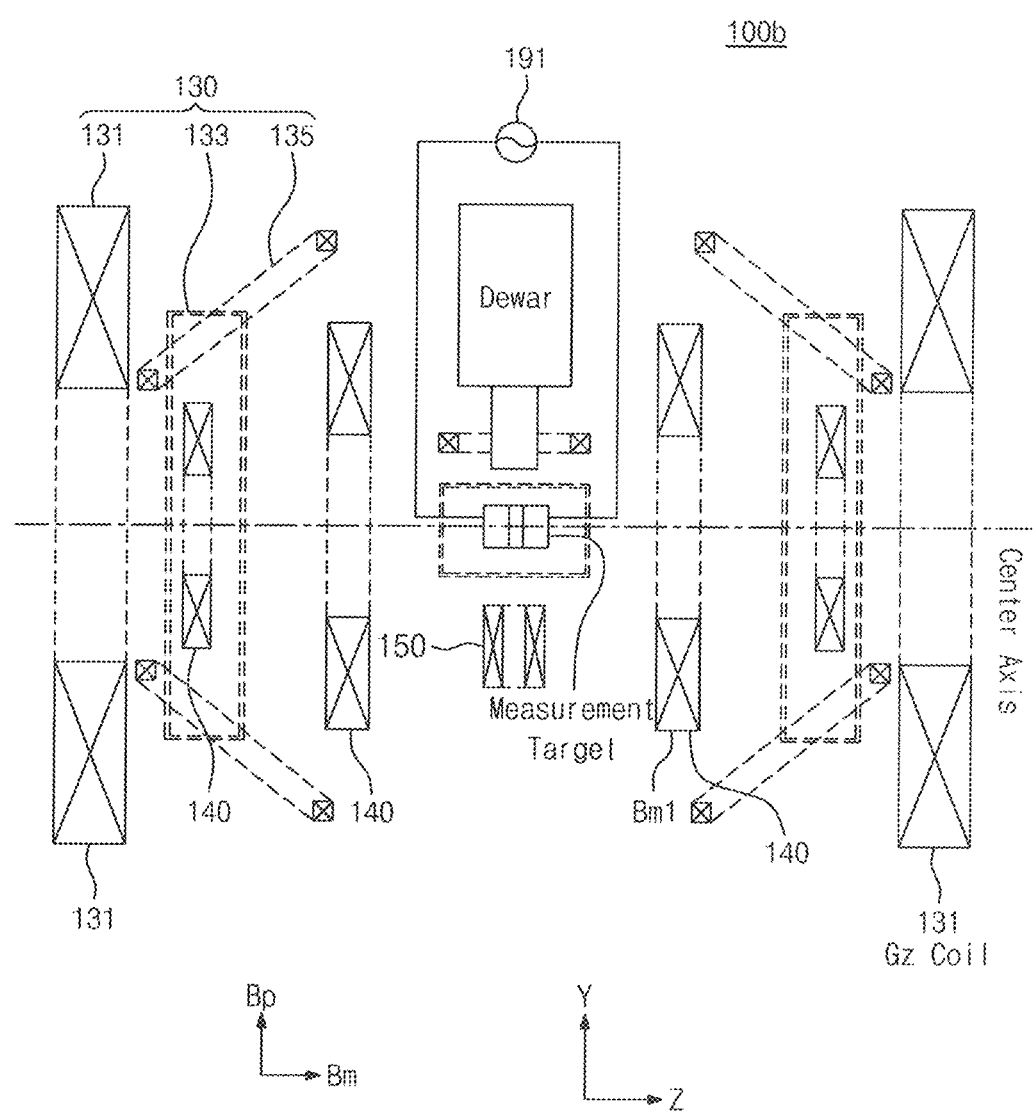
FIG. 17 is a conceptual diagram of an ultra-low field nuclear magnetic resonance device according to another example embodiment of the present disclosure.

FIG. 17 is a conceptual diagram of an ultra-low field nuclear magnetic resonance device according to another example of the present disclosure.

Figure 18:
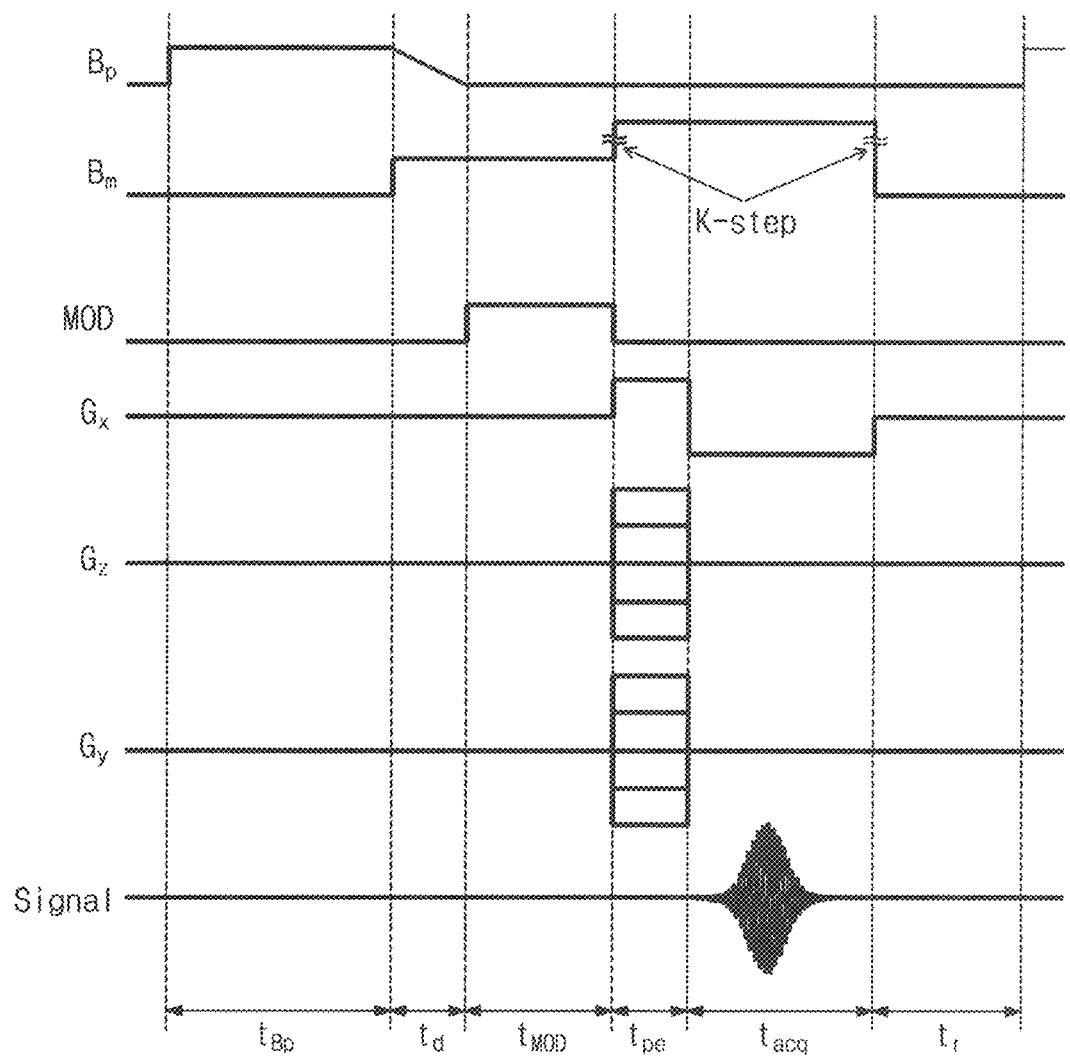
FIG. 18 illustrates a pulse sequence of the ultra-low field nuclear magnetic resonance device in FIG. 17.

FIG. 18 illustrates a pulse sequence of the ultra-low field nuclear magnetic resonance device in FIG. 17.

Referring to FIGS. 17 and 18, an ultra-low field nuclear magnetic resonance device 100b includes an AC power supply 191 configured to supply a current to a measurement target such that a current flows to the measurement target, a magnetic field measurement means 160 disposed close to the measurement target, and a measurement bias magnetic field generation means 140 configured to apply a measurement bias magnetic field corresponding to a proton magnetic resonance frequency of the measurement target. A vibration frequency of the AC power supply 191 matches a proton magnetic resonance frequency of the measurement target, and the magnetic field measurement means 160 measures a nuclear magnetic resonance signal generated from the measurement target.

The pre-polarizing magnetic field generation means 150 generates a pre-polarizing magnetic field to pre-polarize the measurement target. A direction of the pre-polarizing magnetic field may be perpendicular to a direction of the measurement magnetic field. A magnetization direction of the measurement target may be aligned in the direction of the measurement bias magnetic field by reducing the intensity of the pre-magnetization magnetic field through an adiabatic process while the measurement bias magnetic field is applied.

An MREIT imaging pulse sequence is a three-dimensional gradient-echo pulse sequence. The MREIT imaging pulse sequence includes the steps of applying a pre-polarizing magnetic field Bp for an application time $t_{Bp}$ of a pre-polarizing magnetic field Bp, reducing a magnitude of the pre-magnetizing magnetic field Bp through an adiabatic process for a predetermined time $t_d$ while the measurement bias magnetic field Bm is applied, applying a modulated magnetic field $B_{MOD}$, applying gradient magnetic fields Gx, Gy, and Gz while increasing the magnitude of the measurement bias magnetic field Bm, measuring a nuclear magnetic resonance signal for a predetermined time $t_{acq}$, and providing a repetition time $t_r$.

The pre-polarizing magnetic field Bp is adjusted for a predetermined time $t_d$ such that nuclear spins aligned in a direction of the pre-polarizing magnetic field Bp are directed toward the measurement bias magnetic field Bm through the adiabatic process. An abrupt variation of a magnetic field does not change the direction of the nuclear spins aligned in the direction of the pre-polarizing magnetic field Bp. However, when the pre-polarizing magnetic field Bp is reduced with satisfying a specific condition in which the adiabatic process is performed while the measurement bias magnetic field Bm is applied, the nuclear spins, aligned in a direction of the pre-polarizing magnetic field Bp, may rotate in the direction of the measurement bias magnetic field Bm.

A current map may be obtained if an MR image is acquired using an ultra-low field three-dimensional (two-dimensional) gradient-echo signal sequence or an MR image is required through slice selection. This is because an NMR signal is generated by a magnetic field generated by a current. A current density image may be obtained from the current map using a typical deconvolution algorithm. Since the current density is expressed as the product of an electric conductivity and an electric field, an electric conductivity image may be obtained. An electric conductivity image is obtained from a current density image using an algorithm such as a boundary element method (BEM).

As described above, according to an example embodiment, a current image may be acquired by applying a modulated magnetic field when a pre-polarizing magnetic field is in the same direction as a measurement bias magnetic field.

According to an example embodiment, a current image may be obtained when a modulated magnetic field and an excitation magnetic field are applied and a pre-polarizing magnetic field is perpendicular to a measurement bias magnetic field.

According to an example embodiment, a current image may be obtained by applying a modulated magnetic field and through an adiabatic process of a pre-polarizing magnetic field when the pre-polarizing magnetic field is perpendicular to a measurement bias magnetic field.

Although the present disclosure and its advantages have been described in detail, it should be understood that various changes, substitutions and alterations can be made herein without departing from the spirit and scope of the disclosure as defined by the following claims.

What is claimed is:

1. An ultra-low field nuclear magnetic resonance device comprising:
   an AC power supply configured to supply a current to a measurement target in a manner so that the current flows in the measurement target, the measurement target having a proton magnetic resonance frequency;
   a magnetic field measurement part adjacent to the measurement target; and a measurement bias magnetic field generator configured to apply a measurement bias magnetic field corresponding to the proton magnetic resonance frequency of the measurement target,
wherein:
the AC power supply has a first vibration frequency that matches the proton magnetic resonance frequency of the measurement target,
the current in the measurement target produces a modulated magnetic field, and
the magnetic field measurement part is configured to measure a nuclear magnetic resonance signal from the measurement target.

2. The ultra-low field nuclear magnetic resonance device as set forth in claim 1, further comprising:
a pre-polarizing magnetic field generator configured to produce a pre-polarizing magnetic field in a first direction and apply the pre-polarizing magnetic field for an application time to pre-polarize the measurement target,
wherein:
the measurement bias magnetic field has a second direction, and the first direction matches the second direction, and
after the application time, the measurement bias magnetic field generator applies the measurement bias magnetic field, and the current in the modulation target produces the modulated magnetic field.

3. The ultra-low field nuclear magnetic resonance device as set forth in claim 2, wherein the pre-polarizing magnetic field generator comprises a resistive coil, a superconducting coil, a pancake-type coil or a solenoid coil.

4. The ultra-low field nuclear magnetic resonance device as set forth in claim 1, further comprising:
a pre-polarizing magnetic field generator configured to produce a pre-polarizing magnetic field to pre-polarize the measurement target; and
an excitation magnetic field generator configured to switch a magnetization direction of the measurement target,
wherein:
the measurement bias magnetic field has a first direction, and the pre-polarizing magnetic field has a second direction that is perpendicular to the first direction, and
the excitation magnetic field generator rotates the magnetization direction in the first direction.

5. The ultra-low field nuclear magnetic resonance device as set forth in claim 4, wherein:
the excitation magnetic field generator is configured to generate a circularly polarized excitation magnetic field.

6. The ultra-low field nuclear magnetic resonance device as set forth in claim 1, further comprising:
a pre-polarizing magnetic field generator configured to apply a pre-polarizing magnetic field to pre-polarize the measurement target,
wherein:
the measurement bias magnetic field has a first direction, and the pre-polarizing magnetic field generator is configured to produce the pre-polarizing magnetic field in a second direction perpendicular to the first direction,
the pre-polarizing magnetic field has a magnitude, the measurement target has a magnetization direction, and When the measurement bias magnetic field generator applies the measurement bias magnetic field, the pre-polarizing magnetic field generator is configured to adiabatically reduce the magnitude of the pre-polarizing magnetic field so that the magnetization direction of the measurement target is aligned in the first direction.

7. The ultra-low field nuclear magnetic resonance device as set forth in claim 1, further comprising:
a gradient magnetic field generator configured to provide a gradient magnetic field to the measurement target.

8. The ultra-low field nuclear magnetic resonance device as set forth in claim 7, wherein the gradient magnetic field generator comprises a triaxial gradient magnetic field coil.

9. The ultra-low field nuclear magnetic resonance device as set forth in claim 1, wherein the measurement target is a part of a human body.

10. The ultra-low field nuclear magnetic resonance device as set forth in claim 1, wherein the measurement target is an organ in a human body.

11. The ultra-low field nuclear magnetic resonance device as set forth in claim 1, wherein the current is an alternating current that flows to the measurement target by an electrode pad, the alternating current in the measurement target generates the modulated magnetic field, and the modulated magnetic field has a predetermined vibration frequency.

12. The ultra-low field nuclear magnetic resonance device as set forth in claim 11, configured to apply the modulated magnetic field to the measurement target as a pulse for an application time of 30-150 ms.

13. The ultra-low field nuclear magnetic resonance device as set forth in claim 1, wherein the magnetic field measurement part comprises a superconducting quantum interference device.

14. The ultra-low field nuclear magnetic resonance device as set forth in claim 1, wherein the measurement bias magnetic field generator comprises a double Helmholtz coil.

15. The ultra-low field nuclear magnetic resonance device as set forth in claim 1, wherein the modulated magnetic field has a second vibration frequency identical to the proton magnetic resonance frequency of the measurement target.

16. A method for measuring an ultra-low field nuclear resonance image comprising:
applying a pre-polarizing magnetic field to pre-polarize a measurement target, the measurement target having a proton magnetic resonance frequency;
applying a measurement bias magnetic field corresponding to the proton magnetic resonance frequency, the measurement bias magnetic field having a first vibration frequency;
producing a modulated magnetic field in the measurement target by providing an alternating current to the measurement target, the alternating current having a second vibration frequency corresponding to the proton magnetic resonance frequency;
applying a gradient magnetic field to the measurement target;
generating a nuclear magnetic resonance signal from the measurement target;
measuring the nuclear magnetic resonance; and
obtaining a current image of the measurement target using the nuclear magnetic resonance signal,
wherein:
the second vibration frequency corresponds to the first vibration frequency.

17. The method as set forth in claim 16, wherein:
the pre-polarizing, magnetic field has a first direction, the measurement bias magnetic field has a second direction, and applying the pre-polarizing magnetic field further comprises matching the first direction to the second direction, and the modulated magnetic field has a third direction, and the third direction is perpendicular to the second direction.

18. The method as set firth in claim 16, wherein the measurement target has a magnetization direction, the measurement bias magnetic field has a first direction, and the method further comprises:

providing an excitation magnetic field to switch the magnetization direction of the measurement target to the first direction, wherein:

the pre-polarizing magnetic field has a second direction, the pre-polarizing magnetic field aligns the magnetization direction of the measurement target in the second direction, and the second direction is perpendicular to the first direction, and when providing the excitation magnetic field, the excitation magnetic field rotates the magnetization direction of the measurement target from the second direction to the first direction.

19. The method as set forth in claim 18, wherein:

the excitation magnetic field is a circularly polarized excitation magnetic field.

20. The method as set forth in claim 16, wherein:

the pre-polarizing magnetic field has a first direction, the measurement bias magnetic field has a second direction, and the first direction is perpendicular to the second direction, and the measurement target has a magnetization direction, the pre-polarizing magnetic field has a magnitude, and applying the pre-polarizing magnetic field comprises adiabatically reducing the magnitude of the pre-polarizing magnetic field while applying the measurement bias magnetic field.

* * * * *